United States Patent
Baggio et al.

(10) Patent No.: US 7,399,645 B2
(45) Date of Patent: Jul. 15, 2008

(54) CONSTRAINED CIS-DIOL-BORATE BIOCONJUGATION SYSTEM

(75) Inventors: Ricky F. Baggio, Waltham, MA (US); Alison L. Sparks, North Andover, MA (US); Rouh-Rong Juo, Allston, MA (US); Jaime E. Arenas, Lexington, MA (US)

(73) Assignee: Applera Corporation, Bedford, MA (US)

( * ) Notice: Subject to any disclaimer, the term of this patent is extended or adjusted under 35 U.S.C. 154(b) by 221 days.

(21) Appl. No.: 11/126,837

(22) Filed: May 11, 2005

(65) Prior Publication Data

US 2005/0277143 A1    Dec. 15, 2005

Related U.S. Application Data

(60) Provisional application No. 60/570,313, filed on May 12, 2004, provisional application No. 60/578,946, filed on Jun. 10, 2004.

(51) Int. Cl.
G01N 33/547 (2006.01)
G01N 33/543 (2006.01)
G01N 33/532 (2006.01)
C07K 1/10 (2006.01)
C07K 1/13 (2006.01)
C07F 5/02 (2006.01)

(52) U.S. Cl. ............ 436/532; 436/518; 436/543; 530/402; 530/403; 530/406; 530/812; 568/1

(58) Field of Classification Search .......... 436/532, 436/518, 543; 530/402, 403, 406, 812; 585/355, 585/700; 568/1
See application file for complete search history.

(56) References Cited

U.S. PATENT DOCUMENTS

| | | | |
|---|---|---|---|
| 5,227,474 A * | 7/1993 | Johnson et al. ............. 534/558 |
| 5,744,627 A | 4/1998 | Stowolitz et al. |
| 5,777,148 A | 7/1998 | Stowolitz et al. |
| 5,831,046 A | 11/1998 | Stolowitz et al. |
| 5,837,878 A | 11/1998 | Stolowitz et al. |
| 5,847,192 A | 12/1998 | Stolowitz et al. |
| 5,859,210 A | 1/1999 | Stolowitz et al. |
| 5,869,623 A | 2/1999 | Stolowitz et al. |
| 5,872,224 A | 2/1999 | Stolowitz et al. |
| 5,876,938 A | 3/1999 | Stolowitz et al. |
| 5,877,297 A | 3/1999 | Stolowitz et al. |

(Continued)

FOREIGN PATENT DOCUMENTS

EP    0 295 073 A2    12/1988

(Continued)

OTHER PUBLICATIONS

Gamoh, K., et al., "Stability and Reversed-Phase Liquid Chromatographic Studies of Cyclic Boronates," *Anal. Sci.*, 9:549-552 (1993).

(Continued)

*Primary Examiner*—Long V. Le
*Assistant Examiner*—Shafiqul Haq
(74) *Attorney, Agent, or Firm*—Hamilton, Brook, Smith & Reynolds, P.C.

(57) ABSTRACT

The invention pertains to bioconjugation systems comprising sterically constrained cis-diols and borates.

44 Claims, 9 Drawing Sheets
(6 of 9 Drawing Sheet(s) Filed in Color)

U.S. PATENT DOCUMENTS

| | | | |
|---|---|---|---|
| 6,013,783 | A | 1/2000 | Kaiser et al. |
| 6,031,117 | A | 2/2000 | Kaiser et al. |
| 6,075,126 | A | 6/2000 | Stolowitz et al. |
| 6,124,471 | A | 9/2000 | Stolowitz et al. |
| 6,462,179 | B1 | 10/2002 | Stolowitz et al. |
| 6,630,577 | B2 | 10/2003 | Stolowitz et al. |
| 2003/0073243 | A1 | 4/2003 | Law et al. |

FOREIGN PATENT DOCUMENTS

| | | |
|---|---|---|
| WO | WO 00/12540 A1 | 3/2000 |
| WO | WO 01/66567 A2 * | 9/2001 |
| WO | WO 03/102217 A2 | 12/2003 |
| WO | WO 2005/016859 A2 | 2/2005 |

OTHER PUBLICATIONS

Zanette, D., et al., "Evaluation of Phenylboronate Agarose for Industrial-Scale Purification of Erythropoietin From Mammalian Cell Cultures," *J. Biotech.*, 101:275-287 (2003).

Soh, Nobuaki, et al., "Evaluation of Interactions between Monosaccharides and a Stationary Phase Modified with Alkylboronic Acid by Means of a Liquid-Chromatographic Method," *Analytical Sciences*, 18: 1159-1161 (2002).

Westmark, P.R., et al., "Selective Monosaccharide Transport Through Lipid Bilayers Using Boronic Acid Carriers," *J. Am. Chem. Soc.*, 118: 11093-11100 (1996).

Shoji E., et al., "Potentiometric Saccharide Detection Based on the $pK_a$ Changes of Poly(aniline boronic acid)," *J. Am. Chem. Soc.*, 124: 12486-12493 (2002).

Homola, J., et al., "Surface Plasmon Resonance—A Method to Analyze Interfacial Optical Properties and to Develop Biosensors," *Sensors and Actuators* 54: 3-15 (1999).

Gibson, Frank S., et al., "A Practical Synthesis of L-Valyl-pyrrolidine-(2R)-boronic Acid: Efficient Recycling of the Costly Chiral Auxiliary (+)-Pinanediol," *Organic Process Research & Development*, 6: 814-816 (2002).

Matteson, Donald S., et al., "(Alkoxyalkyl)boronic Ester Intermediates for Asymmetric Synthesis," *Organometallics*, 15: 152-163 (1996).

Hiscox, William C., et al., "An Efficient Preparation of R, R)-1,2-Dicyclohexylethane-1,2-diol, a Superior Chiral Director for Synthesis with Boronic Esters," *J. Org. Chem.*, 61: 8315-8316 (1996).

U.S. Appl. No. 11/800,341, by Ricky F. Baggio, Alison L. Sparks, Rouh-Rong Juo and Jamie E. Arenas, filed May 4, 2007.

\* cited by examiner

Association phase  Dissociation phase

CONSTRAINED CIS-DIOL-BORATE BIOCONJUGATION SYSTEM

RELATED APPLICATIONS

This application claims the benefit of U.S. Application No. 60/570,313, filed on May 12, 2004 and U.S. Application No. 60/578,946, filed Jun. 10, 2004. The entire teachings of the above applications are incorporated herein by reference.

INTRODUCTION

Various methods of bioconjugation are known in the art for joining bioactive molecules to other bioactive molecules, assay tags, sensors, solid supports in an assay system, chromatographic columns, and the like. Two complementary elements can be reacted to form a conjugate, e.g., an antibody/antigen, a protein/ligand pair (e.g., streptavidin/biotin), a polynucleotide and its complementary sequence, and the like. Certain attributes are typically desirable for such systems, e.g., conjugation or binding specificity, conjugation reaction rate, conjugation binding strength, convenience of the conjugation reaction, chemical compatibility, and the like. Existing bioconjugation systems, however, typically make trade-offs among these attributes, e.g., one or two attributes being strong and the others being weak. These tradeoffs can limit the applicability of existing bioconjugation systems in various applications of interest. For example, streptavidin/biotin is a selective bioconjugation system but has disadvantages including the size of the streptavidin element (preventing formation of high-density arrays of bioconjugation sites on a solid support or interfering with the detection of smaller bioactive molecules), the sensitivity of the streptavidin element to conditions that can cause denaturation (e.g., pH extremes or conditions used to couple the streptavidin to a solid support or bioactive molecule), and an overall ionic charge of avidin and/or biotin can increase adverse nonspecific binding.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other features and advantages will be apparent from the following description of various embodiments, as illustrated in the accompanying drawings in which like reference characters refer to the same parts throughout the different views. The drawings are not necessarily to scale, emphasis instead being placed upon illustrating the principles of the teachings. The skilled artisan will understand that the drawings, described below, are for illustration purposes only. The drawings are not intended to limit the scope of the present teachings in any way.

In FIG. 6A, the buffer used was 50 mM sodium acetate, 100 mM sodium chloride, pH 5.5. In FIG. 6B, the buffer used was phosphate buffered saline with 0.05% Tween-20, pH 7.4. In FIG. 6C, the buffer used was sodium carbonate-bicarbonate buffer pH 9.4.

DESCRIPTION OF VARIOUS EMBODIMENTS

Figure 1:
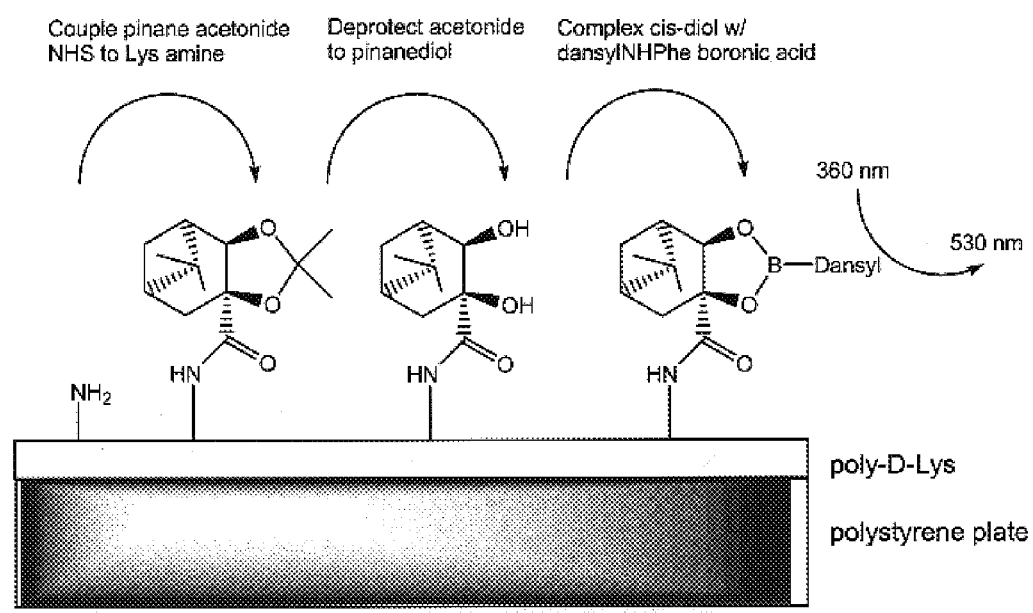
FIG. 1 is a schematic of covalent conjugation of surface-bound pinane diol (bound to poly-D-Lys Plates) with m-dansylaminophenylboronic acid (DAPB).

The present teachings relate to the use of boronate esters formed by covalent bond formation and/or complexation between a boronic acid and a particular type of constrained cis-diol. The formation of stable boronate esters from boronic acid:cis-diol pairs can be used to create a surface for capturing biomolecules and/or subsequently detecting biomolecular interactions. To accomplish the preferential capture of biomolecules on a surface, e.g., a microchip or biochip surface, the surface can be derivatized with a constrained cis-diol and the biomolecule of interest can be derivatized with a boronic acid. The converse can also be employed for biomolecular capture, where the surface is derivatized with boronic acid and the biomolecule is derivatized with a constrained cis-diol. The boronate ester complex can also be used preferentially as a bioconjugation method to unite two functional groups, such as biological or small molecule moieties, either intermolecularly or intramolecularly for detection of function analyses. To accomplish the preferential unification of two functional groups, the first moiety can be derivatized with a boronic acid, and the second moiety can be derivatized with a particular constrained cis-diol. The present invention does not restrict the boronic acid moiety to phenyl boronic acid or related analogues. Any alkyl or aromatic boronic acid with a linker arm for attachment to a surface or a biomolecule can be employed. Also contemplated are constrained cis-diols with a linker arm for surface attachment or biomolecule modification.

The present teachings contemplate the ability to conjugate a biomolecule with high specificity (e.g., with specificity and affinity that can be as high as that between biotin and streptavidin) to either a solid support or to another biomolecule. Also contemplated are various embodiments where surface modification with covalently linked cis-diols can produce a neutral environment because both the borate and the constrained cis-diol can be small, non-reactive organic molecules, and can also be amenable to incorporation into peptide, nucleic acid and peptide nucleic acid synthetic syntheses. Such a surface, lacking either positive or negative charge, can have distinct chemical properties for example, it can have low non-specific biomolecule binding to the large majority of unlabeled proteins and other biomolecules, which can thereby reduce assay noise. Any boronic acid-labeled biomolecule can bind to such a surface with high specificity, even in the presence of unlabeled carrier proteins. Compared to commonly used streptavidin or avidin surfaces, such cis-diol surfaces can have a much higher binding capacity and density due to the small size of the capture molecule.

Also contemplated are various embodiments where a borate surface is formed, where, for example, depending upon the pKa of the immobilized boronic acid, such a surface can exist in either a neutral or negatively charged state. Such borate-modified surfaces can exhibit an affinity for cis-diol-labeled biomolecules, as well as certain carbohydrates (based on polyol geometries).

The present teaching also contemplates various embodiments wherein any application involving biotin/streptavidin bioconjugation can be replaced by bioconjugation with cis-diols/boronic acids, which can 1) reduce noise due to non-specific binding of biomolecules, 2) increase load capacity on a surface, and/or 3) create a neutral or negatively charged surface as needed in assay design.

In some embodiments, the present invention provides for conjugation of a biomolecule with high specificity to either a solid support or to another biomolecule. The conjugation can involve very strong interaction (equivalent in terms of specificity and binding affinity to that of streptavidin:biotin), yet because both the boronic acid and the constrained cis-diol can be small (e.g., in various embodiments less than about 5000 daltons, less than about 2500 daltons, or less than about 1000 daltons), relatively stable organic molecules, they are highly amenable to incorporation into bioactive molecules (e.g., peptide and nucleic acid synthetic syntheses). Also, solid support modification with cis-diols or boronates can produce a charge-neutral surface, which can lead to lower non-specific binding of other molecules on the solid support.

In some embodiments, the present invention provides for conjugation of a biomolecule with specificity to either a solid support or to another biomolecule. In these embodiments, n or n' is greater than 1 and the boronic acid and/or the constrained cis-diol can independently be, for example, in various embodiments less than about 30,000 daltons, less than about 20,000 daltons, or less than about 10,000 daltons.

Further, because the cis-diol:boronate can be small molecules (e.g., compared to streptavidin) this system can have a much higher binding capacity, due to significantly increased capture agent density in conjugates per $cm^2$. In other words, many more small molecules, such as cis-diols or boronic acids, can fit per $cm^2$ compared to biomolecules such as streptavidin or biotin. Increased binding density enables greater detection sensitivities, especially in increasingly smaller assay loci, such as array formats. Such a system can therefore lead to higher assay signals and can also be expected to be stable and exhibit a long shelf life.

By forming a boronic acid surface, certain other advantages can be realized. For example, depending upon the pKa of the immobilized boronic acid, such a surface can exist in either a neutral or negatively charged state under physiological conditions, and changes in pH can adapt the response of the surface to cis-diol binding, binding of other polyols, and nonspecific binding of other molecules.

Also, the constrained cis-diol:boronate system can have significantly stronger binding affinities than salicylhydroxamic acid: phenylboronic acid systems (see, for example, U.S. Pat. Nos. 6,630,577, 6,462,179, 6,124,471, 6,075,126, 6,031,117, 6,013,783, 5,877,297, 5,876,938, 5,872,224, 5,869,623, 5,859,210, 5,847,192, 5,837,878, 5,831,046, 5,777,148, and 5,744,627). The constrained cis-diol:boronate system, where binding affinities are believed to be driven by steric factors can produce significantly stronger binding events with minimal analyte dissociation. The stronger binding affinities of the constrained cis-diol/boronic acid bioconjugation are amenable to surface and chip assay design where clean, robust analyte capture is desired.

These and other features of the present teachings will become more apparent from the description herein. In various embodiments, the particulars of the system, the method, and the compound are further provided below. Each detail provided is contemplated in some embodiments of each of the system, the method, and the compound, separately and in combination.

A bioconjugation system can comprise a sterically constrained cis-diol and a borate represented respectively by:

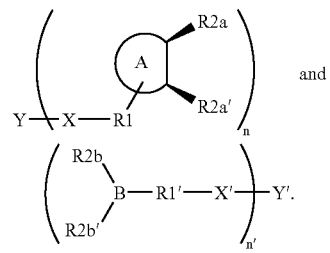

The variables n and n' are to indicate that a corresponding number of the groups in parentheses are attached to the corresponding Y or Y' in parallel, i.e., the groups in parentheses are not representing an n or n'-fold serial oligomer or polymer.

Ring A can be an optionally substituted bicycloalkyl, heterocyclyl or fused bicycloalkyl-heterocyclyl, or Ring A can be an optionally substituted cycloalkyl.

$R^1$ and $R^{1'}$ can be independently an optionally substituted alkyl, alkoxy, alkyl ether, alkyl sulfide, cycloalkyl, heterocyclyl, aryl, heteroaryl, cycloalkylalkyl, heterocyclylalkyl, aralkyl, heteroaralkyl, cycloalkylalkyl ether, heterocyclylalkyl ether, aralkyl ether, heteroaralkyl ether, cycloalkylalkyl sulfide, heterocyclylalkyl sulfide, aralkyl sulfide or heteroaralkyl sulfide linking group.

$R^{2a}$, $R^{2a'}$, $R^{2b}$ and $R^{2b'}$ can each be independently —OH (unprotected) or —O-PG (protected), wherein -PG is an alcohol protecting group selected from optionally substituted esters, ethers, silyl ethers and carbonates. Also, $R^{2a}$ and $R^{2a'}$ can be taken together with the portion of Ring A connecting them to be a protected cis-diol group selected from optionally substituted cyclic acetals, cyclic ketals, and cyclic ortho esters. e.g., a cis-diol can be protected with an acetonide group. $R^{2b}$ and $R^{2b'}$, taken together with the boron to which they are bonded, can be a protected borate group selected from boronates and cyclic boronates. The pairs $R^{2a}$, $R^{2b}$, and $R^{2a'}$, $R^{2b'}$, can be both —O—, whereby the cis-diol and borate to which they are bonded form a conjugate represented by:

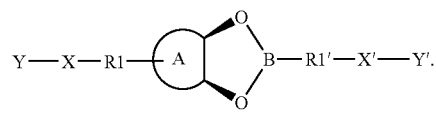

Thus, as used herein, the term "borate" encompasses borates that are unprotected (e.g., when the corresponding $R^{2b}$ or $R^{2b'}$ is —OH) protected (e.g., when $R^{2b}$ and $R^{2b'}$, taken together with the boron to which they are bonded, can be a protected borate group selected from boronates and cyclic boronates), and conjugated (e.g., as in the above structural formula).

Also, as used herein, the term "cis-diol" encompasses cis-diols that are unprotected (e.g., when the corresponding $R^{2a}$ or $R^{2a'}$ is —OH) protected (e.g., when the corresponding $R^{2a}$ or $R^{2a'}$ is —O-PG, or when $R^{2a}$ and $R^{2a'}$ can be taken together with the portion of Ring A connecting them to be a protected cis-diol group), and conjugated (e.g., as in the above structural formula).

Further, the definitions herein are provided such that the "constrained cis-diol" is not a saccharide. As used herein, the term "saccharide" means monosaccharides such as fructose, mannitol, galactose, glucose, mannose, allose, altrose, talose, tagatose, Psicose, ribose, arabinose, sorbitol, and oligomers and polymers of any one or any combination of the preceding monosacharrides.

X and X' can be independently a bond, —O—, —S—, —C(O)—, —C(O)O—, —S(O)—, —OSO$_2$—, —S(O$_2$)O—, —SO$_2$—, —NR$^3$—, —NR$^3$C(O)—, —C(O)NR$^3$C—, —R$^3$NNR$^3$O$_2$—, —SO$_2$NR$^3$NR$^3$—, —NR$^3$SO$_2$—, —SO$_2$NR$^3$—, —CR$^3_2$C(O)NR$^3$—, —NR$^3$C(O)CR$^3_2$—, —CR$^3_2$C(O)—, —C(O)CR$^3_2$—, —R$^3$NNR$^3$—, —NR$^3$NR$^3$—, —R$^3$NNR$^3_2{}^+$—, —NR$^3_2{}^{+NR3}$—, —CR$^3_2$Ph—, —PhCR$^3_2$—, —C(NR$^3$)NR$^3$—, or —NR$^3$C(NR$^3$)—.

Each R$^3$ can be independently —H, alkyl, alkoxy, aryloxy or arylalkoxy.

Y and Y' can be independently a bioactive molecule, a covalently attached solid support, or a self assembled monolayer (SAM)-inducing solid support wherein at least one of Y and Y' is the bioactive molecule. For example, when Y or Y' is a solid support or a self assembled monolayer (SAM)-inducing solid support, the corresponding n or n' can be an integer from 10 to 10$^{10}$. For example, when Y is one of the solid supports, n is an integer from about 10 to about 10$^{10}$; when Y' is one of the solid supports, n' can be an integer from about 10 to about 10$^{10}$. When Y or Y' is a biomolecule, the corresponding n or n' can be an integer from 1 to about 10.

A method of preparing a conjugate represented by:

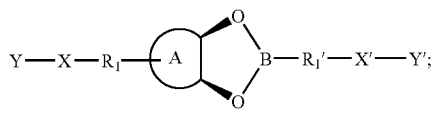

comprises reacting a sterically constrained cis-diol and a borate represented respectively by:

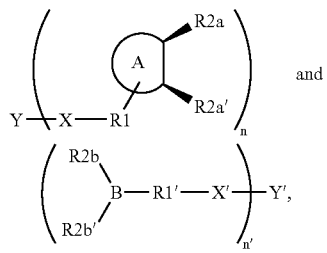

under conditions suitable for reaction between the constrained cis-diol and the borate, thereby forming the conjugate. Suitable reaction conditions can be found in the Examples. Conjugates between sterically constrained cis-diol and a borate have been observed experimentally at pH 5.5 (50 mM sodium acetate, 100 mM sodium chloride buffer), FIG. 6A, and at pH 7.4 (phosphate buffered saline with 0.05% Tween-20), FIG. 3 and FIG. 6B, and at pH 9.4 (200 mM carbonate-bicarbonate buffer), FIG. 6C. In the method, Ring A, R$^1$, R$^{1'}$, R$^{2a}$, R$^{2a'}$, R$^{2b}$, R$^{2b'}$, R$^3$, X, X', Y, Y', n, and n' are as provided above for the bioconjugation system.

A sterically constrained cis-diol compound for bioconjugation can be represented by:

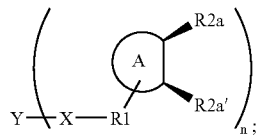

wherein Ring A, R$^1$, R$^{2a}$, R$^{2a'}$, R$^3$, and X are as provided above for the bioconjugation system.

Y can be a bioactive molecule and n can be an integer from 1 to about 200, generally 1 to about 100, or typically 1 to about 10. Y can be a solid support or a self assembled monolayer (SAM)-inducing solid support and n can be an integer from about 10 to about 10$^{10}$. The variable n can be 1 and —Y—X together can be —S—, wherein two cis-diols form a disulfide dimer represented by:

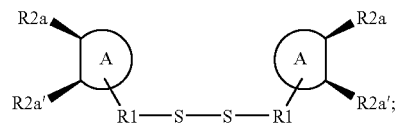

wherein each variable is independently as defined above. The variable n can be 1 and —Y—X together can be —OH, —SH, halogen, —OR$^5$, —C(O)OR$^5$, —O(O)CR$^5$, —NR$^5$R$^6$, or —N-heterocyclyl, wherein R$^5$ and R$^6$ are independently optionally substituted alkyl, cycloalkyl, heterocyclyl, aryl, heteroaryl, cycloalkylalkyl, heterocyclylalkyl, aralkyl, or heteroaralkyl.

In various embodiments, for each bioactive molecule, the corresponding n or n' can be greater than 1, e.g., there can be a plurality of cis-diols or borates for each bioactive molecule.

In various embodiments, for each bioactive molecule, the corresponding n or n' can be 1, e.g., there can be one cis-diol or one borate for each bioactive molecule.

When for each bioactive molecule, the corresponding n or n' is 1, the conjugate can be a stable conjugate, for example, the conjugate represented by:

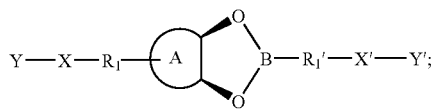

As used herein, a conjugate that is stable is one wherein in aqueous 0.10 M phosphate buffer at 25° C. and pH 7.4, the conjugate can have a dissociation rate of less than about $1\times10^{-4}$ s$^{-1}$. In various embodiments, the stable conjugate can have a dissociation rate of less than about $1\times10^{-5}$ s$^{-1}$. In some embodiments, the stable conjugate can have a dissociation rate of less than about $1\times10^{-6}$ s$^{-1}$. In other embodiments, the stable conjugate can have a dissociation rate of less than about $1\times10^{-7}$ s$^{-1}$. In some embodiments, the conjugate can have an association rate of greater than about 1 M$^{-1}$s$^{-1}$.

In various embodiments, at least one of Y and Y' is the solid support or the self assembled monolayer (SAM)-inducing solid support. For example, Y can be the bioactive molecule and Y' can be the solid support or the self assembled monolayer (SAM)-inducing solid support. Y' can be the bioactive molecule and Y can be the solid support or the self assembled monolayer (SAM)-inducing solid support.

In various embodiments, Y is the solid support and Y' is the bioactive molecule. In some embodiments, Y' is the solid support and Y is the bioactive molecule.

As used herein, "support", "solid support", or "SAM-inducing solid support" refers to any solid phase material. Solid support encompasses terms such as "resin", "synthesis support", "solid phase", "surface" and/or "membrane". A solid support can be composed of optionally substituted organic polymers, e.g., polyalkylene (e.g., polyethylene, polypropylene), polyvinylene, polystyrene, polyethylene oxide, nitrocellulose, polyvinyl acetate, polyvinyl chloride, polyvinyl dichloride, polyfluoroalkylene (e.g., polyfluoroethylene), polyamides (e.g., polyacrylamide, poly(hexamethylene adipamide) and the like), polydialkylsiloxane (e.g., polydimethylsiloxane), and the like, as well as co-polymers and grafts thereof. A solid support can also be inorganic, such as glass (e.g., silicate glass, borate glass, indium tin oxide, controlled-pore-glass (CPG), and the like), silica, quartz, or reverse-phase silica and the like. The configuration of a solid support can be in the form of: one or more beads, spheres (e.g., microspheres), or particles (e.g., granules, nanoparticles); a gel, a membrane, a surface, a film, a porous matrix (e.g., nonwoven support or supports with channels or pores, e.g., porous glasses, sol gels, zeolites, and the like), or interior surface of a microchannel. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

In some embodiments, one of Y and Y' is the solid support or the SAM-inducing solid support and the solid support can have a conductive layer (e.g., metal, conducting glass (e.g., indium tin oxide), and the like, typically metal) for surface plasmon resonance. The solid support or the SAM-inducing solid support can comprise gold, silver, platinum, aluminum, or copper. In some embodiments, the solid support is a nanoparticle comprising cadmium sulfide, cadmium selenide, cadmium telluride, silicon, or gallium arsenide. In some embodiments, the solid support comprises optionally substituted polyalkylene (e.g., polyethylene, polypropylene), polyvinylene, polystyrene, polyethylene oxide, nitrocellulose, polyvinyl acetate, polyvinyl chloride, polyvinyl dichloride, polyfluoroalkylene (e.g., polyfluoroethylene), polyamide (e.g., polyacrylamide, poly(hexamethylene adipamide) and the like), polydialkylsiloxane (e.g., polydimethylsiloxane), and the like, as well as co-polymers and grafts thereof; glass (e.g., silicate glass, borate glass, indium tin oxide, controlled-pore-glass (CPG), and the like), silica, or quartz.

In various embodiments, when one of Y and Y' is the solid support or the SAM-inducing solid support and the solid support includes a conductive layer for surface plasmon resonance, the method further comprises directing light to the conductive layer and measuring a surface plasmon resonance wavelength in order to determine an extent of conjugation by measuring a change in the surface plasmon resonance wavelength before and after formation of the conjugate. The light is directed to the conductive layer in a wavelength range between about 400 nanometers (nm) and about 1200 nm at the conductive layer, at an incident angle greater than a total internal reflectance angle at the solid support, to create a surface plasmon resonance condition at the solid support surface. Typically, the light is in a wavelength range between about 820 nm and 920 nm.

As used herein "array" refers to a predetermined spatial arrangement of reaction sites, e.g., bioconjugation sites present on a solid support or in an arrangement of vessels. Certain array formats can be referred to as a "chip" or "biochip" (M. Schena, Ed. Microarray Biochip Technology, Bio-Technique Books, Eaton Publishing, Natick, Mass. (2000). An array can comprise a low-density number of addressable locations, e.g., 2 to about 12, medium-density, e.g., about a hundred or more locations, or a high-density number, e.g., a thousand or more. An array or chip can be a geometrically-regular shape that allows for fabrication, handling, placement, stacking, reagent introduction, detection, and storage. An array or chip can be irregularly shaped. An array or chip can be configured in a row and column format, with regular spacing between each location. An array or chip can be configured in a row and column format, with irregular spacing. Alternatively, the locations may be bundled, mixed, or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

In various embodiments, an array can be constructed by preparing the conjugate at a plurality of spatially distinct reaction sites on the solid support. The sites can be located in a regular array (e.g., at the vertices of a square grid) or an irregular, e.g., random array. Typically, the reaction sites are located in a regular array, such as may be provided by a printing mechanism, an automated pin-spotting mechanism, and the like. Generally, each spatially distinct reaction site in the array can be an average diameter of between about 5 μm and about 1000 μm. In typical arrays, the spatially distinct reaction sites in the array can be in a surface density of between about 12 sites per $cm^2$ and about 50,000 sites per $cm^2$.

Some embodiments comprise preparing the conjugate at two or more reaction sites in the array to be compositionally distinct, e.g., the conjugate at each of the two or more sites is different in one or more aspects such as concentration, chemical structure, associated bioactive molecule, and the like. Two compositionally distinct sites can also mean the same or different sites measured at different times. The method can comprise contacting a first site with the cis-diol or the borate having the bioactive molecule, in an composition distinct from that employed at a second site. The method can comprise contacting a first site with a first cis-diol or borate containing a first bioactive molecule and contacting a second site with a second cis-diol or borate containing a second bioactive molecule. Some embodiments can comprise determining the extent of conjugation at the first and the second site, e.g., by determining an extent of conjugation by measuring a change in the surface plasmon resonance wavelength between the two compositionally distinct sites.

In some embodiments, when the solid support can be configured as a plurality of particles, beads, microspheres, nanoparticles, granules, and the like, the distinct reaction sites on the solid support can be one or more reaction sites, typically one, on each individual solid support. In some such embodiments, a plurality of compositionally distinct reaction sites can be prepared by repeatedly conjugating one of a library of distinct bioactive molecules with a portion of reaction sites (e.g., particles) to create separate portions of compositionally distinct reaction sites, and then combining them to result in a plurality of compositionally distinct reaction sites, e.g., resulting in a library of bioactive molecules conjugated to distinct particles.

The bioactive molecule can be any biologically relevant molecule of interest, for example, the bioactive molecule can comprise one or more nucleic acids, polynucleic acids, amino acids, peptides, proteins, peptide nucleic acids, hormones, cofactors, fatty acids, carbohydrates, polysaccharides, glycopeptides, glycoproteins; peptidoglycans; glycolipids, cyclitols, prenols, terpenoids, steroids, folates, carotenoids, retinoids, tocopherols, lignans, quinines, isoprenoids, tetrapyrroles, lipids, prostaglandins, immunoglobulins, glycolipids, lipoproteins, neurotransmitters, biometabolites, pharmaceuticals environmental toxins, small organic molecules (e.g., pharmaceuticals) and the like. Molecules in the preceding list can be obtained from commercial sources, generated by chemical synthesis by combinatorial synthesis methods known to the art, extracted from natural sources, and the like. In some embodiments, the bioactive molecule includes a library of bioactive molecules, e.g., a plurality of biologically or chemically distinct bioactive molecules of one or more classes of molecules from the preceding list, typically one class. Typically, a library of bioactive molecules can be a plurality of molecules generated by chemical synthesis or combinatorial chemistry, each generally having a molecular weight from about 100 daltons to about 5000 daltons.

Screening of libraries of small molecules for binding or other interaction with target biomolecules of interest has typically been done in solution, with compounds attached to beads, and recently, with libraries attached to microarrays (see, for example, MacBeath, G. (2001) Genome Biology 2(6): comment 2005.1-2005.6; Lam, K S., and Renil, M (2002). Curr. Op. Chem. Biol. 6:353-358; and Khandurina J,. and Guttman, A. (2002) Curr. Op. Chem. Biol. 6:359-366). In microarrays, the small molecules of the library can have a common functional group, which can be reacted with a suitable functional group on the surface to form a stable bond. Functional groups described for immobilization of small molecule libraries include thiols (MacBeath, et al. (1999) JACS 121:7967-7968), alcohol (Hergenrother, et al. (2000) JACS 122:7849-7850), amino-oxy group (Falsey, et al. (2001) Bioconjug Chem 12:346-353) and phenols (Barnes-Seeman, et al. (2003) Angew Chem Int Ed 42:2376-2379. The entire teachings of each reference in this paragraph are incorporated herein by reference.

In various embodiments, the bioconjugation system can include a library of bioactive compounds, i.e., a plurality of reaction sites on the solid support can be prepared to have chemically or biologically distinct bioactive molecules conjugated at each site. The library can be a collection of any bioactive molecules as described herein, but can typically be a collection of small molecules synthesized by combinatorial methods. In such libraries, each bioactive molecule can have any size, though typically each molecule is in a size range between about 100 and about 5000 daltons. The plurality of spatially distinct reaction sites on the support can each be a distinct support (e.g., when the solid support is configured as a plurality of particles, beads, granules, and the like) or a spatially distinct reaction site on a single solid support, e.g., an array as described herein. Typically, the bioactive molecule library can be prepared as an array on a single solid support.

Such bioconjugation libraries can be used for any purpose known to the art for compound libraries. For example, a small compound library array can be tested for interaction, e.g., chemical reaction, specific binding, or nonspecific binding, and the like, of its bioactive molecules to a target of interest, such as a therapeutic target protein, peptide, or nucleic acid using any of many methods known to the art such as surface plasmon resonance, fluorescence, luminescence, staining, enzyme-linked immunoabsorbent assay, radioactivity based methods, and the like. Thus, in some embodiments, the bioconjugation system comprising a bioactive molecule library array as described herein is combined with a target bioactive molecule of interest and the combination is assayed for specific binding between the target and each bioactive molecule in the library.

In various embodiments, the library of bioactive molecules can be prepared by chemical synthesis or combinatorial synthesis, for example, bioactive molecules prepared by such methods can, for example, be coupled to the cis-diols or borates herein by synthetic methods described in the Examples. In some embodiments, precursors or intermediates to library molecules can be prepared by chemical synthesis or combinatorial synthesis and be coupled to the cis-diols or borates herein by synthetic methods described in the Examples, and the cis-diol:borate bioconjugates formed; subsequently, the coupled precursors or intermediates can be further modified by chemical synthesis or combinatorial synthesis methods known to the art to further diversify molecules of the library.

Thus, in various embodiments, the bioconjugation system further comprises a plurality of each of the sterically constrained cis-diols and the borates; wherein at least one of Y or Y' is, independently for each corresponding cis-diol or borate, a distinct bioactive molecule selected from a plurality of distinct bioactive molecules (e.g., a bioactive molecule library), and each corresponding n or n' is an integer from 1 to 3, whereby the bioconjugation system comprises a library of distinct bioactive molecules. Thus, in some embodiments, at least one of Y or Y' represents the library of bioactive molecules. Typically, the other of Y or Y' is the solid support comprising a plurality of spatially distinct reaction sites, wherein a plurality of the reaction sites can be prepared to be compositionally distinct by conjugation with distinct bioactive molecules from the library. Generally, the solid support is in the form of covalently attached particles, a single covalently attached solid support, or the self-assembled monolayer (SAM) inducing support, or more typically, the solid support is a single covalently attached solid support, e.g., an array as described herein. Thus, in some embodiments, the bioconjugation system is a bioactive molecule library array, wherein Y represents, independently for each cis-diol, a distinct bioactive molecule from the bioactive molecule library (e.g., Y collectively represents the bioactive molecule library) and Y' represents, independently for each borate, a spatially distinct reaction site in an array (e.g., Y' collectively represents a spatially distinct array of cis-diols on a solid support). In other embodiments of the bioactive molecule library array, Y' represents, independently for each borate, a distinct bioactive molecule from the bioactive molecule library (e.g., Y' collectively represents the bioactive molecule library), and Y represents, independently for each cis-diol, a spatially distinct reaction site in an array (e.g., Y collectively represents a spatially distinct array of cis-diols on a solid support). In the embodiments described in this paragraph, the variables n and n' can independently be an integer of between 1 to 3, or more typically, n and n' can each be 1. Typically, each bioactive molecule in the library is from about 100 daltons to about 5000 daltons, and the library is typically constructed by chemical synthesis or combinatorial synthesis methods.

In some embodiments, the structures and variables of the cis-diol, borate, and conjugate are as provided above, with the following modifications.

In some embodiments, $R^{1'}$ can be an optionally substituted aryl, aralkyl, C1-C16 alkyl, or C1-C16 alkoxy group. In some embodiments, $R^{1'}$ can be C2-C16 alkyl ether, C1-C16 alkoxy or C1-C16 alkyl.

In various embodiments, the cis-diol can be represented by:

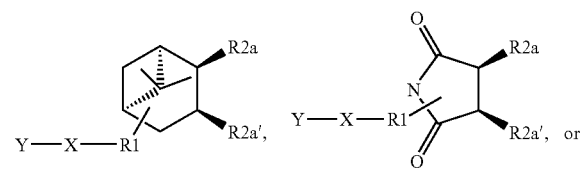

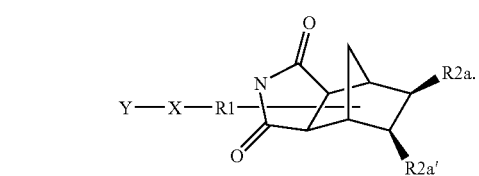

In some embodiments, the cis-diol can be represented by:

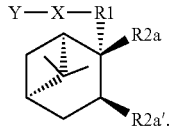

Here, $R^1$ can be as described above, or can be C2-C16 alkyl ether, C1-C16 alkoxy or C1-C16 alkyl; and X can be —NH—, —C(O)NH—, —NHC(O)— or —S—. Or, X can be —S— and $R^1$ can be —(CH$_2$)$_2$O (CH$_2$)$_8$— or —(CH$_2$)$_{11}$—. In some embodiments, —X—$R^1$— can be —(CH$_2$)S—. In various embodiments, $R^{2a}$ and $R^{2a'}$ can independently be —OH or —O-PG, or $R^{2a}$ and $R^{2a'}$, can be taken together with the portion of the ring connecting them to be a protected cis-diol group as noted above, e.g., a cis-diol protected as an acetonide group. In some embodiments, $R^{2a}$ and $R^{2a'}$ can be —OH.

These cis-diols can form a conjugate with borates as represented by:

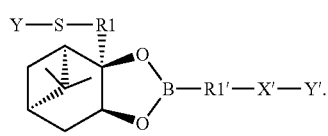

Here, $R^1$ can be as defined above, or can be C6-C12 alkyl, or can be C1-C3 alkyl. In some embodiments, $R^1$ can be —(CH$_2$)—, e.g., the conjugate is represented by:

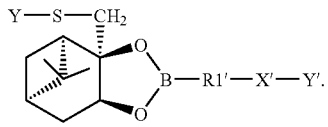

In some embodiments, these cis-diols can form a conjugate with borates as represented by:

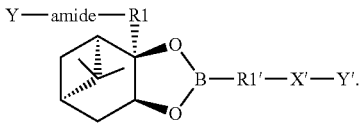

Here, $R^1$ can be as defined above, or can be C6-C12 alkyl, or can be C1-C3 alkyl. "Amide" can be —NHC(O)— or —C(O)NH—. In some embodiments, $R^1$ can be —(CH$_2$)—, e.g., the conjugate is represented by:

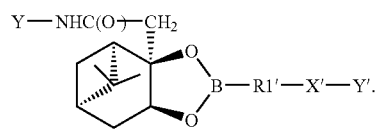

In some embodiments, the cis-diol can be represented by:

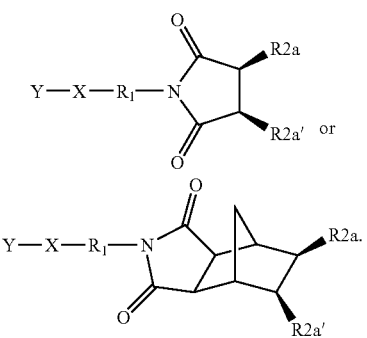

Here, $R^1$ can be as defined above. In some embodiments, $R^1$ can be C1-C4 alkoxy or C1-C4 alkyl and X can be —C(O)O— or amide. In various embodiments, $R^{2a}$ and $R^{2a'}$ can independently be —OH or —O-PG, or $R^{2a}$ and $R^{2a'}$ can be taken together with the portion of the ring connecting them to be a protected cis-diol group as noted above, e.g., a cis-diol protected as an acetonide group. In some embodiments, $R^{2a}$ and $R^{2a'}$ can be —OH.

In various embodiments, cis-diols can form a conjugate with the borate as represented by:

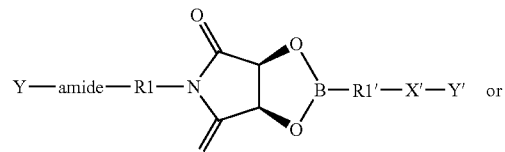

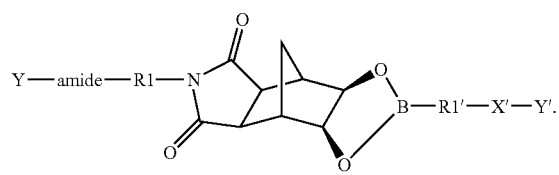

"Amide" can be —NHC(O)— or —C(O)NH—.

In some embodiments of the compound, —Y—X together can be —S—, wherein two cis-diols form a disulfide dimer represented by:

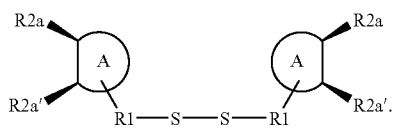

In some embodiments, —Y—X together can be —OH, —SH, halogen, —OR$^5$, —C(O)OR$^5$, —O(O)CR$^5$, —NR$^5$R$^6$ or —N-heterocyclyl. In some embodiments, X can be —S—.

In various embodiments, the cis-diol, unprotected, can be one of:

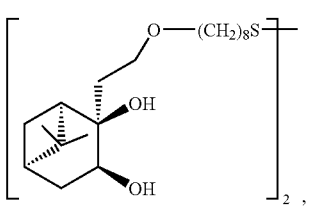

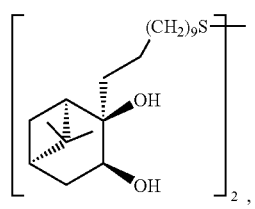

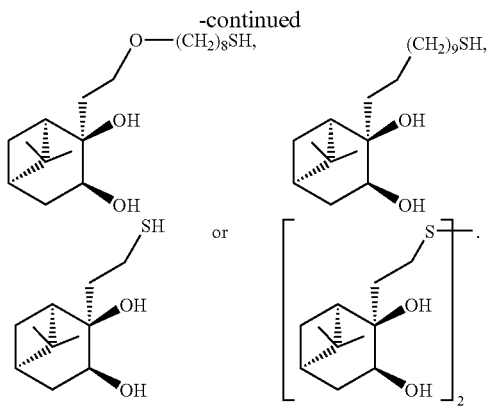

In some embodiments, the cis-diol, protected by an acetonide group, can be one of:

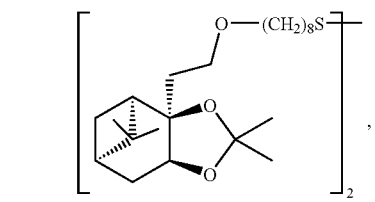

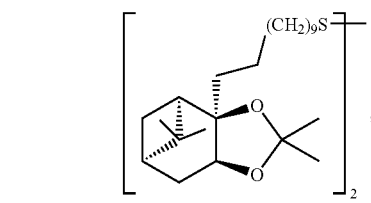

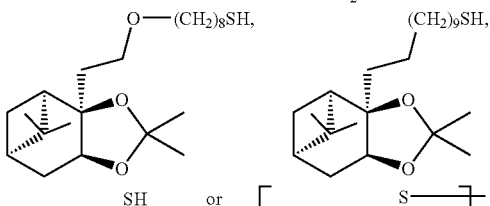

In some embodiments, the cis-diol, unprotected or protected by an acetonide group, can be one of:

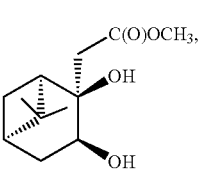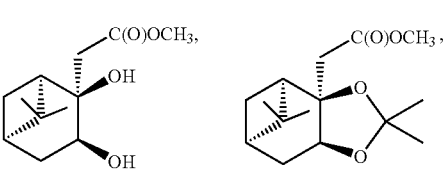

In some embodiments, the cis-diol, unprotected or protected by an acetonide group, can be one of:

[chemical structures]

In some embodiments, the cis-diol, protected by an acetonide group, can be:

[chemical structure]

As used herein, a "constrained" cis-diol is a cyclic structure wherein steric or cyclic constraints cause the diol —OH groups to be held in a relatively fixed aspect to each other, whereby the conjugation reaction with a borate produces a conjugate with the specificity and/or affinity taught in various embodiments. For example, in the constrained cis-diol represented by Ring A in some embodiments, the diol —OH groups, (represented by $R^{2a}$ and $R^{2a'}$) are held in various aspects relative to each other by virtue of being bound to an optionally substituted bicycloalkyl, heterocyclyl or fused bicycloalkyl-heterocyclyl.

As used herein, —PG is an alcohol protecting group for example, optionally substituted esters, ethers, silyl ethers and carbonates. Suitable alcohol protecting groups are well known in the art; see, for example, Greene T W and Wuts P G M, Protective Groups in Organic Synthesis, $3R^d$ ed., Wiley, NY (1999), the entire teachings of which are incorporated herein by reference.

As used herein, cyclic acetals, cyclic ketals, and cyclic ortho esters can be formed with the cis-diol as diol protecting groups, e.g., the acetonides in structures 4-8 in the synthetic examples. Suitable diol protecting groups are well known in the art; see, for example, Greene T W and Wuts P G M, Protective Groups in Organic Synthesis, $3R^d$ ed., Wiley, NY (1999), the teachings of which, that pertain to hydroxyl group protection, are incorporated herein by reference.

As used herein, the term "borate" can mean any typical state of a borate derivative, e.g., the boric acid —$B(OH)_2$, salts, hydrates, and/or solvates thereof, and/or boronate esters, e.g., alkyl esters, aromatic esters, e.g., catechol esters, and the like. Typical boric acid protecting groups, e.g., borate/boronate esters, are well-known in the art; see, for example, Ferrier R J, *Adv. Carbohydr. Chem. Biochem.* 1978, 35:31; Brooks C J W et al., *Adv. Mass Spectrom.* 1978, 7B:1578; Knapp D R, Handbook of Analytical Derivatisation Reactions, Wiley, NY (1979); Greene T W and Wuts P G M, Protective Groups in Organic Synthesis, $3R^d$ ed., Wiley, NY (1999), the teachings of which, that pertain to hydroxyl group protection, are incorporated herein by reference.

The teachings herein do not restrict the borate to phenyl boronic acid or related analogues. Any alkyl or aromatic borate with a linker arm for attachment to a surface or a biomolecule can be employed. For example, commercially available boronic acids for use in this manner include, e.g.:

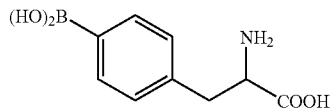

Aldrich #51,268-0 (Sigma Aldrich, St. Louis, Mo.) and

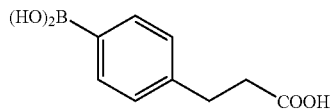

Lancaster Synthesis #17485 (Lancaster Synthesis, Windham, N.H.).

As used herein, the term "linking group", (e.g., the linking groups represented by $R^1$, $R^{1'}$, X, X', and the like) means any chemical group that connects two or more other chemical groups.

The term "alkyl" (e.g., the alkyl groups represented by $R^1$, $R^{1'}$, $R^3$, and the like), used alone or as part of a larger moiety (e.g., aralkyl, alkoxy, alkylamino, alkylaminocarbonyl, haloalkyl), is a straight or branched non-aromatic hydrocarbon which is completely saturated. Typically, a straight or branched alkyl group has from 1 to about 20 carbon atoms, generally from 1 to about 16 if not otherwise specified, Examples of suitable straight or branched alkyl group include methyl, ethyl, n-propyl, 2-propyl, n-butyl, sec-butyl, tert-butyl, pentyl, hexyl, heptyl, octyl, nonyl, decyl, undecyl, dodecyl, terdecyl, tetradecyl, pentadecyl, hexadecyl, heptadecyl, octadecyl, nonadecyl, icosyl, and the like. The term "alkenyl" means alkyl groups with one or more units of unsaturation resulting in one or more double bonds, e.g., butenyl, pentadienyl, hexadecenyl, and the like. The term "alkynyl" means alkyl groups with one or more units of unsaturation resulting in one or more triple bonds, e.g., butynyl, hexadecynyl, and the like.

The term "cycloalkyl group" (e.g., the cycloalkyl groups represented by Ring A) can be a cyclic alkyl group having from 3 to about 10 carbon atoms, generally from 5 to 6. Examples of suitable cycloalkyl groups include cyclopropyl, cyclobutyl, cyclopentyl, cyclohexyl, cycloheptyl and cyclooctyl. The term cycloalkenyl includes cycloalkyl groups having one or more units of unsaturation resulting in a double bond, e.g., cyclopentenyl, cyclohexenyl, and the like.

The term "aryl" group, (e.g., the aryl groups represented by $R^1$ and $R^{1'}$, and the like) refers to carbocyclic aromatic groups such as phenyl, naphthyl, tetrahydronaphthyl, anthracyl, and the like.

The term "heteroaryl" group (e.g., the heteroaryl groups represented by $R^1$ and $R^{1'}$, and the like) refers to heteroaromatic groups, for example imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, tetrazolyl, benzo[1,3]dioxolyl, 2,3-dihydro-benzo[1,4]dioxine, benzopyrimidyl, benzopyrazyl, benzofuranyl, indolyl, benzothienyl, benzoxazolyl, benzoisooxazolyl, benzothiazolyl, benzoisothiazolyl, quinolinyl, isoquinolinyl, benzimidazolyl, tetrahydroquinolinyl, and tetrahydroisoquinolinyl. Generally, aryl and heteroaryl groups comprise phenyl and pyridyl. The term "Ph" indicates a phenyl or a phenylene group, e.g., phenylene in —$CR^3_2Ph$— in X and X'.

The term "nonaromatic heterocycle" and "heterocyclyl" (e.g., the heterocyclyl groups represented by $R^1$ and $R^{1'}$, and the like) refers to non-aromatic ring systems typically having three to eight members, generally five to six, in which one or more ring carbons, generally one to four, are each replaced by a heteroatom such as N, O, or S. Examples of non-aromatic heterocyclic rings include 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothienyl, 3-tetrahydrothienyl, N-morpholinyl, 2-morpholinyl, 3-morpholinyl, 4-morpholinyl, N-thiomorpholinyl, 2-thiomorpholinyl, 3-thiomorpholinyl, 4-thiomorpholinyl, 1-pyrrolidyl, 2-pyrrolidyl, 3-pyrorolidyl, 1-piperazyl, 2-piperazyl, 1-piperidyl, 2-piperidyl, 3-piperidyl, 4-piperidyl, 4-thiazolidyl, diazolonyl, N-substituted diazolonyl, 1-pthalimidyl, azetidyl, aziridyl, oxaziridyl, oxazolidyl, isooxazolidyl, thiazolidyl, isothiazolidyl, oxazinanyl, thiazinanyl, azepanyl, oxazepanyl, and thiazepanyl. Typically, the nonaromatic heterocycle groups represented by $R^1$ and $R^{1'}$ can be optionally substituted pyrrolidyl, piperidyl, piperazyl, morpholinyl, and thiomorpholinyl, or generally, unsubstituted piperidyl or morpholinyl.

An "_____oxy" group (e.g., alkoxy, cycloalkoxy, aryloxy, aralkyloxy, and the like) refers to the indicated group when connected through an intervening oxygen atom, e.g., alkoxy groups include methoxy, ethoxy, n-propoxy, 2-propoxy, n-butoxy, sec-butoxy, tert-butoxy, pentoxy, hexoxy, heptoxy, octoxy, nonoxy, decoxy, undecoxy, dodecoxy, terdecoxy, tetradecoxy, pentadecoxy, hexadecoxy, heptadecoxy, octadecoxy, nonadecoxy, icosoxy, and the like. Examples of cycloalkoxy groups include cyclopropoxy, cyclobutoxy, cyclopentoxy, cyclohexoxy, cycloheptoxy and cyclooctoxy. Examples of aryloxy and aralkyloxy groups include phenoxy and benzyloxy.

A "_____sulfide group (e.g., alkyl sulfide, cycloalkyl sulfide, aryl sulfide, aralkyl sulfide, cycloalkylalkyl sulfide, heterocyclylalkyl sulfide, heteroaralkyl sulfide and the like)

refers to the indicated group when connected through an intervening sulfur atom, e.g., analogous to "_____oxy" groups described herein.

An "alkyl ether" (e.g., in alkyl ether, cycloalkylalkyl ether, heterocyclylalkyl ether, aralkyl ether, heteroaralkyl ether, and the like) indicates an alkyl group that is interrupted by one or more, typically one, oxygen atoms, e.g., groups of the formula —(CH$_3$)$_i$O(CH)$_k$—, wherein i and k are positive integers greater than zero and i+k is between 2 to 20, generally between 2 to 16. An "alkylthioether" is an analogous group wherein the oxygen is replaced by sulfur.

An "_____alkyl" group (e.g., cycloalkylalkyl, heterocyclylalkyl, aralkyl, heteroaralkyl, and the like) indicates the named group is connected through an intervening alkyl group, e.g., benzyl, —CH$_2$H$_2$-pyridine, and the like.

The terms "optionally substituted" means that the named group can be unsubstituted or can be substituted with one or more groups, provided the groups do not substantially interfere with the conjugation methods.

"Optionally halogenated", as used herein, includes the respective group substituted with one or more of —F, —Cl, —Br, or —I.

The terms "alkanoyl", "aroyl", and the like, as used herein, indicates the respective group connected through an intervening carbonyl, for example, —(CO)CH$_2$CH$_3$, benzoyl, and the like. The terms "alkanoyloxy", "aroyloxy", and the like, as used herein, indicates the respective group connected through an intervening carboxylate, for example, —O(CO)CH$_2$CH$_3$, —O(CO)C$_6$H$_5$, and the like.

The disclosed compounds can contain one or more chiral centers. For example, in Ring A, the carbons bonded to R$^{2a}$ and R$^{2a'}$ are each a chiral center. The presence of chiral centers in a molecule gives rise to stereoisomers. For example, a pair of optical isomers, referred to as "enantiomers", exist for every chiral center in a molecule. A pair of diastereomers exists for every chiral center in a compound having two or more chiral centers. Where the structural formulas do not explicitly depict the stereochemistry of each chiral center it is to be understood that these formulas encompass enantiomers free from the corresponding optical isomer, racemic mixtures, mixtures enriched in one enantiomer relative to its corresponding optical isomer, a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s).

The term "derivative" refers to compounds that have a common core structure, and are substituted with various groups as described herein.

A line across a bond in a ring, for example, the line from R$^1$ across Ring A, indicates that the represented bond can be connected to any substitutable atom in the ring.

A "substitutable atom" is any atom such as nitrogen or carbon that can be substituted by replacing a hydrogen atom bound to the atom with a substituent. A "substitutable ring atom" in a ring is any ring atom, e.g., a carbon or nitrogen, which can be substituted.

Suitable substituents are those that do not substantially interfere with the conjugation activity of the disclosed compound. A compound or group can have one or more substituents, which can be identical or different. Examples of suitable substituents for a substitutable carbon atom in an alkyl, cycloalkyl, cycloalkenyl, non-aromatic heterocycle, aryl, or heteroaryl group include —OH, halogen (—Br, —Cl, —I and —F), —R, —OR, —CH$_2$R, —CH$_2$CH$_2$R, —OCH$_2$R, —CH$_2$OR, —CH$_2$ CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —NH$_2$, —NHR, —N(R)$_2$, —COOR, —CH$_2$COOR, —CH$_2$CH$_2$COOR, —CHO, —CONH$_2$, —CONHR, —CON(R)$_2$, —NHCOR, —NRCOR, —NHCONH$_2$, —NHCONRH, —NHCON(R)$_2$, —NRCONH$_2$, —NRCONRH, —NRCON(R)$_2$, —C(=NH)—NH$_2$, —C(=NH)—NHR, —C(=NH)—N(R)$_2$, —C(=NR)—NH$_2$, —C(=NR)—NHR, —C(=NR)—N(R)$_2$, —NH—C(=NH)—NH$_2$, —NH—C(=NH)—NHR, —NH—C(=NH)—N(R)$_2$, —NH—C(=NR)—NH$_2$, —NH—C(=NR)—NHR, —NH—C(=NR)—N(R)$_2$, —NRH—C(=NH)—NH$_2$, —NR—C(=NH)—NHR, —NR—C(=NH)—N(R)$_2$, —NR—C(=NR)—NH$_2$, —NR—C(=NR)—NHR, —NR—C(=NR)—N(R)$_2$, —SO$_2$NH$_2$, —SO$_2$NHR, —SO$_2$NR$_2$, —SH, —SO$_k$R (k is 0, 1 or 2) and —NH—C(=NH)—NH$_2$. Each R is independently an alkyl, cycloalkyl, benzyl, aromatic, heteroaromatic, or phenylamine group that is optionally substituted. Generally, R is unsubstituted. In addition, —N(R)$_2$, taken together, can also form a substituted or unsubstituted heterocyclic group, (e.g., as for NR$^c$$_2$, and NR$^j$$_2$) such as pyrrolidinyl, piperidinyl, morpholinyl and thiomorpholinyl. Examples of substituents on group represented by R include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a heterocyclic group or heteroaromatic group include —R', —N(R')$_2$, —C(O)R', —CO$_2$ R, —C(O)C(O)R', —C(O)CH$_2$ C(O)R', —SO$_2$R', —SO$_2$ N(R')$_2$, —C(=S)N(R')$_2$, —C(=NH)—N (R')$_2$, and —NR' SO$_2$R'. R' is hydrogen, an alkyl, alkoxy, cycloalkyl, cycloalkoxy, phenyl, phenoxy, benzyl, benzyloxy, heteroaromatic, or heterocyclic group that is optionally substituted. Examples of substituents on the groups represented by R' include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. Generally, R' is unsubstituted.

EXEMPLIFICATION

Aspects of the present teachings may be further understood in light of the following examples, which should not be construed as limiting the scope of the present teachings in any way.

Synthetic Examples

The compounds defined above can be made by the procedures provided in the following synthetic examples. All reagents can be obtained from Sigma-Aldrich, St. Louis, Mo., unless otherwise noted.

Synthesis of Pinane Acetonide with Carboxylic Acid Linker

Scheme 1 shows preparation of pinanediol derivative 6, masked as an acetonide, with an acetic acid linker attachment for a solid support or biomolecule. Oxidation of nopol acetate with osmium tetroxide yielded the cis-diol. After acetonization of the diol and deacylation, the side chain alcohol was oxidized to a carboxylic acid.

Scheme 1: Synthesis of Pinane Acetonide with Carboxylic Acid Linker

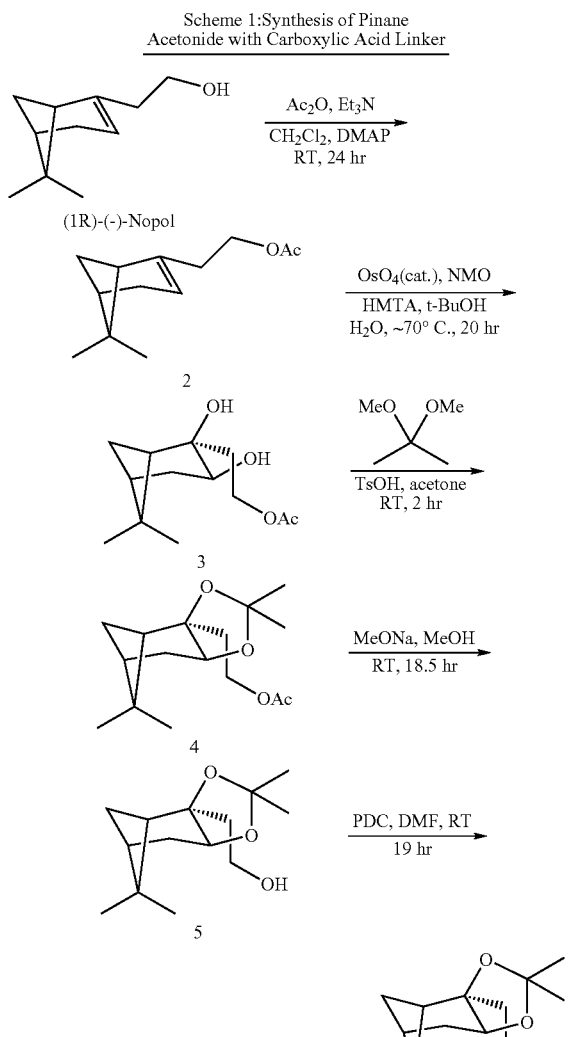

Synthetic Protocol:

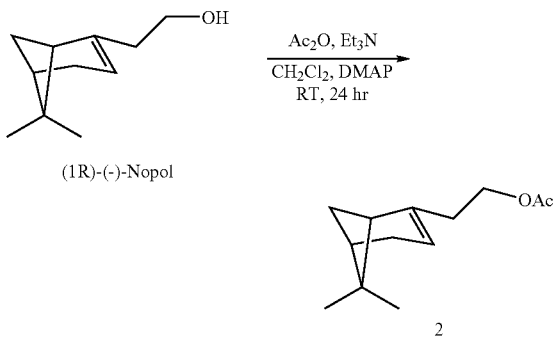

Pinene Acetate 2: To a mixture of (1R)-(−)-nopol (10 g, 59 millimole (mmol)), triethylamine (12.3 ml, 88 mmol, 1.5 equiv) and dimethylaminopyridine (DMAP. 16.5 mg) in 100 ml of CH$_2$Cl$_2$, acetic anhydride (6.7 ml, 71 mmol, 1.2 equiv) was added dropwise via syringe. The resulting mixture was stirred at room temperature under an argon atmosphere. Thin layer chromatography (TLC) after two hours showed the reaction was nearly complete, but was allowed to stir overnight. In the morning, the reaction mixture was washed with 50% NaHCO$_3$ solution and brine, dried over anhydrous Na$_2$SO$_4$ and concentrated. The crude product was purified over a silica gel plug, eluting with 2~5% ethyl acetate (EtOAc) in hexanes, to afford the pinene acetate 2 as a colorless oil (12.4 g, >100%). IR (CHCl$_3$): 3030, 2990, 2920, 2838, 1730, 1470, 1435, 1385, 1368, 1250, 1128, 1032, and 886 cm$^{-1}$. $^1$H NMR (400 MHz, CDCl$_3$): δ 5.30 (br s, 1H), 4.02-4.13 (m, 2H), 2.34-2.40 (m, 1H), 2.16-2.32 (m, 4H), 2.02-2.12 (m, 2H), 2.04 (s, 3H), 1.28 (s, 3H), 1.15 (d, J=8.9 Hz, 1H), 0.83 (s, 3H).

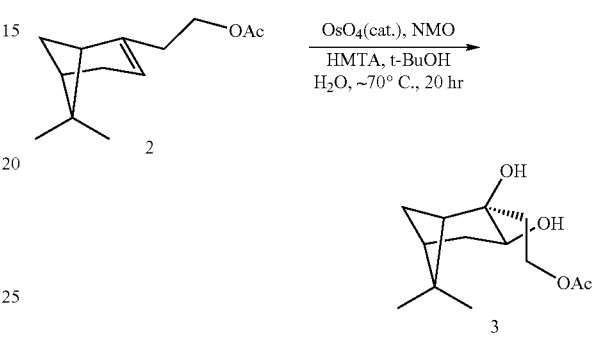

Pinanediol Acetate 3: A 250 ml round-bottomed flask was purged with argon gas three times, and then heated under argon atmosphere. After cooling back to room temperature, the flask was charged with a mixture of 4-methylmorpholine-N-oxide (NMO, 1.2 g, 10.5 mmol, 1.05 equiv), t-butanol (21.25 ml), water (3.75 ml) and hexamethylenetetraamine (HMTA, 3.9 g, 27.6 mmol, 2.8 equiv). Pinene acetate 2 (2.1 g, 10 mmol) was added to the mixture, followed by osmium tetroxide stock solution (40 mg/ml H$_2$O, 0.875 ml., 0.14 mmol, 0.014 equiv). The resulting light tan mixture was heated to 71° C. in 23 minutes and maintained at 68~75° C. for 20 hours. The reaction mixture was cooled back to room temperature and stirred with 30 ml of 10% NaHSO$_3$ solution for 30 minutes; no color changed was noticed.

The mixture was extracted with 50% EtOAc/hexanes two times. The combined organic extract was washed with 10% NaHSO$_3$ solution and water, dried over anhydrous Na$_2$SO$_4$ and concentrated to afford the crude product as a tan oil (2.85 g). The pinanediol acetate 3 was purified by silica gel chromatography, eluting with 5~50% EtOAc/hex, to yield a nearly colorless oil (2.03 g, 84%) containing a small amount of a less polar pinane-keto-alcohol acetate byproduct. IR (CHCl$_3$): 3450, 3000, 2927, 2870, 1730, 1475, 1455, 1388, 1370, 1230, 1128, 1042, and 605 cm$^{-1}$. $^1$HNMR (400 MHz, CDCl$_3$): δ 4.26-4.38 (m, 2H), 4.03-4.09 (m, 1H), 3.15 (s, 1H, OH), 2.89 (d, J=6.2 Hz, 1H, OH), 2.46-2.54 (m, 1H), 2.18-2.26 (m, 1H), 2.10 (t, J=5.8 Hz, 1H), 2.06(s, 3H), 1.92-2.05 (m, 2H), 1.79-1.87 (m, 1H), 1.63-1.70 (m, 1H), 1.38 (d, J=10.4 Hz, 1H), 1.27 (s, 3H), 0.94 (s, 3H).

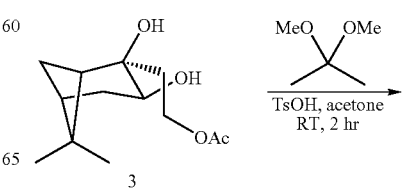

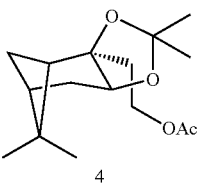

4

Pinane Acetonide Acetate 4: To a solution of pinanediol acetate 3 (9.3 g, 38.5 mmol) in 110 ml of acetone, 2,2-dimethoxypropane (9.5 ml, 77 mmol, 2 equiv) was added dropwise via syringe at room temperature under argon atmosphere. To the mixture was then added catalytic p-toluene sulfonic acid (TsOH, 17.5 mg) and the reaction was stirred for 2 hours. Ten drops of triethylamine were added via pipette and the solution was concentrated by rotary evaporation to produce a yellow residue. The crude product was purified by a silica gel plug, eluting with 3~6% EtOAc/hex, to give the slightly impure pinane acetonide acetate 4 as a colorless oil (9.1 g, 83%). IR (CHCl$_3$): 2995, 2945, 2877, 1732, 1460, 1384, 1373, 1238, 1125, 1044, 1029 and 886 cm$^{-1}$. $^1$HNMR (400 MHz, CDCl$_3$): δ 4.19-4.31 (m, 2H), 4.13 (d, J=7.2 Hz, 1H), 2.01-2.25 (m, 5H), 2.04 (s, 3H), 1.87-2.0 (m, 2H), 1.63 (d, J=9.8 Hz, 1H), 1.48 (s, 3H), 1.39(s, 3H), 1.29 (s, 3H), 0.88 (s, 3H).

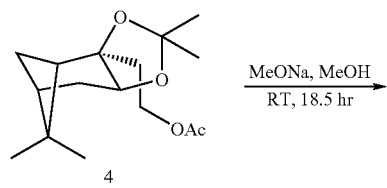

Pinane Acetonide Alcohol 5: To a solution of pinane acetonide acetate 4 (9.0 g, 38.5 mmol) in 75 ml of anhydrous methanol (MeOH), a solution of 4.37 M sodium methoxide (MeONa) in MeOH (0.36 ml, 0.05 equiv) was added dropwise via syringe. The reaction vessel was sealed with a septum and stirred at room temperature for 25 hours until the reaction was nearly complete. Upon removal of volatiles on a rotary evaporator, a milky colored gum was obtained. The crude product was purified by silica gel plug, eluting with 10~30% EtOAc/hex, to produce the slightly impure pinane acetonide alcohol 5 as a light yellow gum (7.5 g, 97%), containing impurities above and below the product spot by TLC. IR (CHCl$_3$): 3500, 2992, 2942, 2878, 1455, 1385, 1375, 1243, 1123, 1050, 1028, 1002, 978, 926 and 885 cm$^{-1}$. $^1$HNMR (400 MHz, CDCl$_3$): δ 4.15 (d, J=6.9 Hz, 1H), 3.85-3.95 (m, 1H), 3.65-3.75 (m, 1H), 2.89 (dd, J=8.2, 2.3 Hz, 1H), 2.28-2.31 (m, 1H), 1.89-2.21 (m, 6H), 1.67 (d, J=10.4 Hz, 1H), 1.49 (s, 3H), 1.44 (s, 3H), 1.29 (s, 3H), 0.83 (s, 3H).

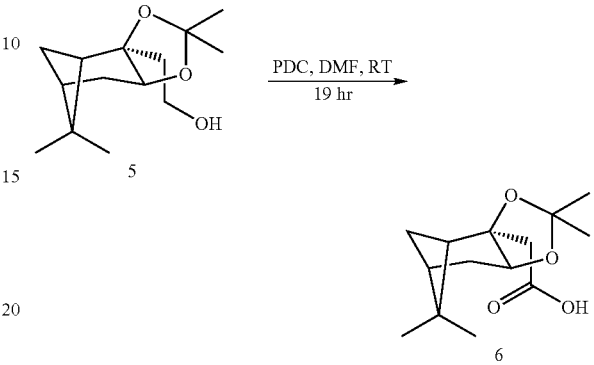

Pinane Acetonide Carboxylic Acid 6: To a solution of pinane acetonide alcohol 5 (2 g, 8.3 mmol) in 57 ml of anhydrous N,N'-dimethylformamide (DMF), powdered pyridinium dichromate(PDC) (15.7 g, 41.6 mmol, 5 equiv) was added in small portions under an argon atmosphere. TLC monitoring of the reaction showed all of the starting material was consumed after 19 hours of stirring at room temperature, but a small amount of intermediate aldehyde was still present. Water (100 ml) was added, and the dark brown mixture was extracted five times with EtOAc (100 ml). The combined organic extract was washed with H$_2$O, and dried over anhydrous Na$_2$SO$_4$. Most of the brown color in organic solution was removed by filtration on a cake of silica gel, to afford 4.0 g of a light brown oil after concentration of the filtrate. Residual pyridine and dimethyl formamide (DMF) were pumped off under vacuum with gentle heating, until the crude product weight stabilized at 2.7 g. The product was purified by silica gel chromatography, eluting with 10~20% acetone/CH$_2$Cl$_2$, to yield the 1$^{st}$ crop of pinane acetonide carboxylic acid 6, as a light yellow solid (1.4 g, 67%). Re-chromatography of impure fractions provided additional acid 6 (0.3 g, 16%). IR (CHCl$_3$): 3550, 3010-3400 (broad), 2990, 2942, 2878, 1770, 1715, 1455, 1387, 1378, 1235, 1186, 1149, 1039, 1000, 975, 920, 870 and 818 cm$^{-1}$. $^1$H NMR (400 MHz, CDCl$_3$): δ 4.21 (d, J=7.0 Hz, 1H), 2.93 (d, J=15 Hz, 1H), 2.82 (d, J=14.1 Hz, 1H), 2.35-2.43 (m, 1H), 2.13-2.27 (m, 2H), 1.91-2.05 (m, 2H), 1.65 (d, J=10.7 Hz, 1H), 1.55 (s, 3H), 1.48 (s, 3H), 1.32 (s, 3H), 0.90 (s, 3H). The carboxylic acid proton was not observed.

Coupling of Pinane Acetonide via Activated Ester

One-step and two-step coupling methods were developed to couple an activated ester of the pinane acetonide carboxylic acid with amines. O—(N-succinimidyl)—N,N, N', N'-tetramethyluronium tetrafluoroborate (TSTU) activation in aqueous acetonitrile afforded the N-hydroxysuccinimido (NHS) ester, which could be isolated or reacted in situ with amines. The coupling proceeded quickly in moderate yields, which were not optimized (66%), and appeared to tolerate a variety of solvent mixes (DMF, DMF/H$_2$O 4:1, DMF/dioxane/H$_2$O 2:2:1, CH$_3$ $_{CN,}$ $_{CH3}$CN/H$_2$O 4:1). Model coupling methods were demonstrated with n-butylamine in synthetic protocols detailed below.

Scheme 2: Coupling of Pinane Acetonide via Activated Ester a: 2-Step with BuNH₂

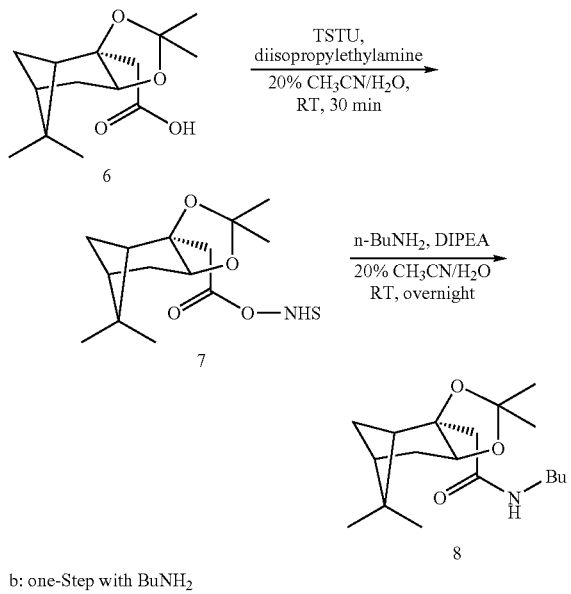

b: one-Step with BuNH₂

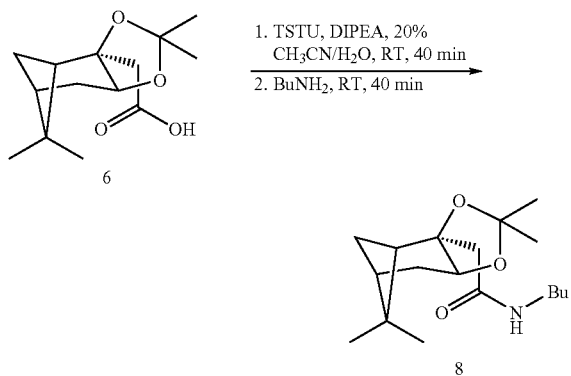

Synthetic Protocol:

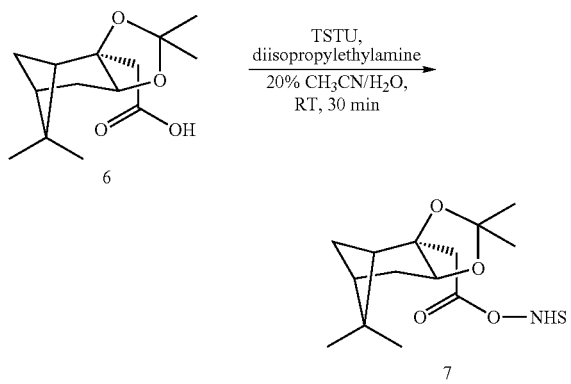

Pinane Acetonide NHS Ester 7: To a mixture of the slightly impure acid 6 (341.4 mg, 1.34 mmol) and TSTU (606 mg, 2 mmol, 1,5 equiv) in 10 ml of 20% water/CH₃CN, diisopropylethylamine (DIPEA, 0.7 ml, 4 mmol, 3 equiv) was added dropwise via syringe. After 30 minutes of stirring at room temperature, TLC of the light yellow mixture showed the reaction was complete. After evaporation of CH₃CN at reduced pressure, the residue was partitioned between EtOAc and water. The aqueous phase was extracted three times with EtOAc, and the combined organic extracts were then washed with brine, dried over anhydrous Na₂SO₄ and evaporated. The crude material was purified by silica gel chromatography, eluting with 50 ml of 3% acetone in CH₂Cl₂, to give the NHS ester 7 as an off-white powder (309.7 mg, 66%). IR (CHCl₃): no acid absorption at 3500 cm⁻¹; the C=O absorptions at 1822 (m), 1793 (m) and 1745 (s) cm⁻¹. ¹H NMR (400 MHz, CDCl₃): δ 4.22 (d, J=7.2 Hz, 1H), 3.10 (d, J=14.4 Hz, 1H), 3.05 (d, J=14.4 Hz, 1H), 2.83 (br s, 4H), 2.58 (m, 1H), 2.14-2.25 (m, 2H), 2.0 (dd, J=14.4, 3.9 Hz, 1H), 1.91-1.96 (m, 1H), 1.64 (d, J=10.6 Hz, 1H), 1.52 (s, 3H), 1.48 (s, 3H), 1.31 (s, 3H), 0.91 (s, 3H).

The same NHS ester 7 could be prepared in the same fashion in other solvent systems: DMF (22.7 mg, 77%), DMF/p-dioxane/water (2:2:1, 66%), 20% water in DMF (66%), CH₃CN (good yield by TLC) and 20% water in ethanol (poor yield by TLC).

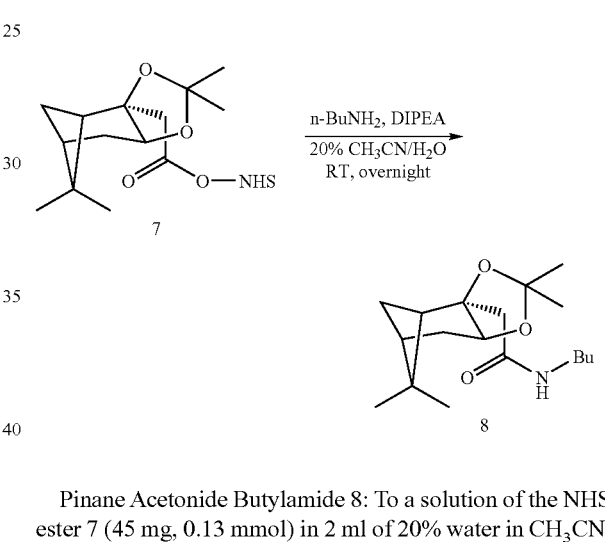

Pinane Acetonide Butylamide 8: To a solution of the NHS ester 7 (45 mg, 0.13 mmol) in 2 ml of 20% water in CH₃CN, n-butylamine (20 μl, 0.19 mmol, 1.5 equiv) and diisopropylethylamine (67 μl, 0.38 mmol, 3 equiv) were added sequentially at room temperature. The mixture was stirred overnight (20 hours). Volatile components were removed by rotary evaporation; the residue was partitioned between CH₂Cl₂ and brine. The aqueous phase was extracted three times with CH₂Cl₂. The combined organic extracts were washed with water, dried over anhydrous Na₂SO₄ and concentrated to give the amide 8 as a light brown gum (28.4 mg, 72%). The amide 8 can be prepared directly in a one-pot reaction between the acid 6 and butylamine in the presence of TSTU without isolation of the NHS ester 7, as shown by the next reaction.

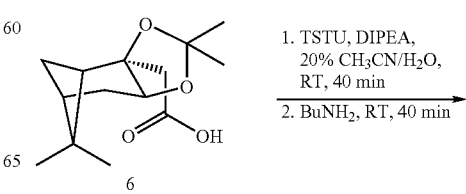

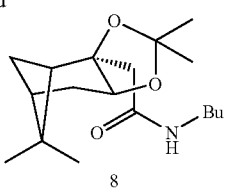

8

One-Pot Synthesis of Pinane Acetonide Butylamide 8: To a mixture of the acid 6 (90.7 mg, 0.36 mmol) and TSTU (161 mg, 0.53 mmol, 1.5 equiv) in 2 ml of 20% water/CH$_3$CN, diisopropylethylamine (0.19 ml, 1.07 mmol, 3 equiv) was added dropwise. The resulting mixture was stirred at room temperature for 40 minutes and then treated with n-butylamine (44 μl, 0.45 mmol, 1.25 equiv) dropwise. TLC analysis showed that the reaction was complete in 40 minutes. Volatile components were removed by rotary evaporation; the residue was partitioned between EtOAc and brine. The aqueous phase was extracted three times with EtOAc. The combined organic extract was washed with water, dried over anhydrous Na$_2$SO$_4$ and concentrated. The crude material was purified by silica gel chromatography, eluting with 3~5% acetone in CH$_2$Cl$_2$ to give the amide 8 as a colorless gum (73 mg, 66%). IR (CHCl$_3$): 3400, 2990, 2937, 2838, 1660, 1535, 1387, 1377, 1210-1235, 1156, 1118, 1035 and 917 cm$^{-1}$. $^1$H NMR (400 MHz, CDCl$_3$): δ 6.69 (br s, 1H, N—H), 4.13 (d, J=7.1 Hz, 1H), 3.16-3.31(m, 2H), 2.73 (s, 2H), 2.11-2.23 (m, 3H), 1.90-2.0 (m, 2H), 1.62 (d, J=9.7 Hz, 1H), 1.52 (s, 3H), 1.46-1.51 (m, 2H), 1.44 (s, 3H), 1.29-1.40 (m, 2H), 1.27 (s, 3H), 0.93 (t, J=7.3 Hz, 3H), 0.92 (s, 3H).

Acetonide Deprotection: Synthetic Protocol:

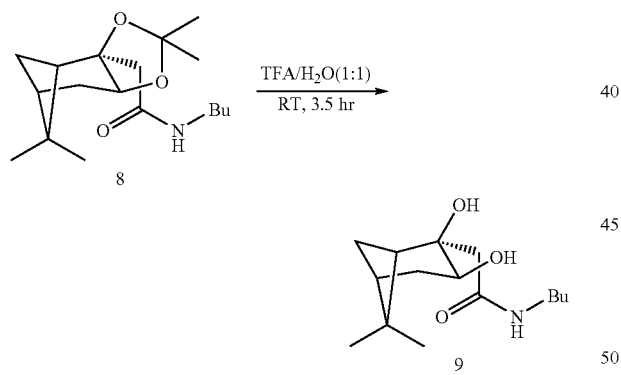

Pinanediol Butylamide 9: Pinane acetonide butylamide 8 (107 mg, 0.35 mmol) was stirred with a 1:1 mixture of trifluoroacetic acid (TFA)/water (3 ml) at room temperature. The reaction was monitored by TLC and showed about 75% conversion to the cis-diol after 2 hours, then the reaction stalled and the intensity of a new spot between starting material and product started to build up. The unknown byproduct may be formed from fragmentation of the pinane ring in product 9 under the acidic condition. The optimal reaction time was about 3.5 hours. The reaction mixture was neutralized with saturated NaHCO$_3$ solution, and then was extracted 3 times with 50% EtOAc/hex. The combined organic extract was washed with H$_2$O, dried over anhydrous Na$_2$SO$_4$ and concentrated. Residual unreacted starting material 8 and byproduct from the pinanediol butylamide 9 was not removed by silica chromatography. IR (CHCl$_3$): 3455, 3390, 3000, 2960, 2930, 2875, 1647, 1530, 1463, 1385, 1140, 1117, 1054, 1033 and 1018 cm$^{-1}$.

Synthesis of Pinanediol C2 Thiol/Disulfide

Scheme 3 shows methods using nopol as the starting material to make a pinanediol analogue with a 2C thiol chain. This compound can be a candidate for surface modification via SAMs on gold. The 2C thiol derivative can serve as a model for developing general methods to synthesize pinanediols with longer (C11+) aliphatic thiol side chains. Conversion of nopol to an alkyl halide (Cl or Br), followed by oxidation to the cis-diol and displacement of the halide by (TMSi)S$^-$ (((CH$_3$)$_3$Si)S$^-$) at room temperature gave the pinanediol 2C thiol/disulfide mixture in 3 steps under mild conditions.

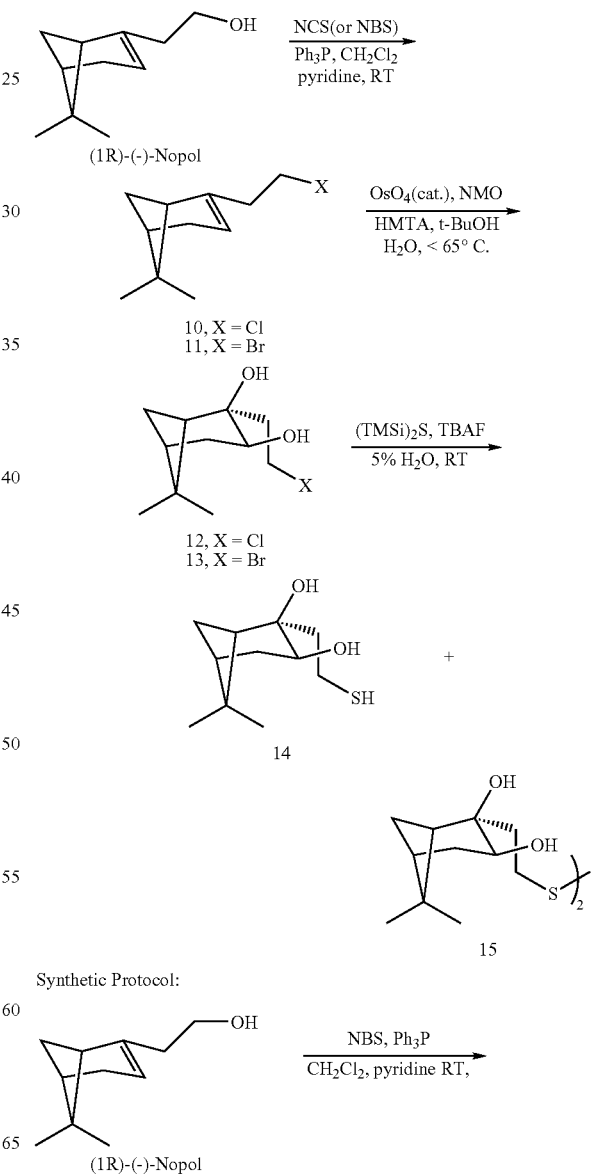

Synthetic Protocol:

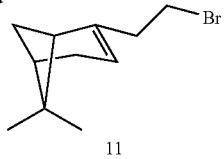

11

Pinene Bromide 11: To a solution of triphenylphosphine (6.1 g, 23.4 mmol, 2 equiv) in 45 ml of $CH_2Cl_2$ at 0° C., orange powdered N-bromosuccinimide (NBS, 4.2 g, 23.4 mmol, 2 equiv) was added in small portions under an argon atmosphere. The resulting deep red mixture was stirred at room temperature for 30 minutes and then 1 ml pyridine was added. The color darkened to reddish-brown, and nopol (2 ml, 117 mmol) was added to the mixture dropwise via syringe over 10 minutes. TLC showed the reaction was complete in 3 hours. The mixture was diluted with 40 ml of hexanes and filtered through a coarse silica gel plug. 100 ml of 5% EtOAc/hex was used to flush the column; the combined filtrate was concentrated to generate 6.12 g of wet solid. Suspension of the solid in 100 ml hexane precipitated white crystalline succinimide, which was removed by filtration. The filtrate was concentrated to yield 2.95 g of a slightly yellow oil. The crude product was further purified by silica gel plug, eluting with hexanes, to give the pinene bromide 11 as a colorless oil (2.6 g, 97%). IR ($CHCl_3$): 2993, 2923, 2840, 1470, 1448, 1437, 1386, 1370, 1268, 1083, 956 and 636 cm$^{-1}$. $^1$H NMR (400 MHz, CDCl$_3$): δ 5.33 (s with fine splittings, 1H), 3.31-3.42 (m, 2H), 2.48-2.56 (m, 2H), 2.33-2.41 (m, 1H), 2.14-2.32 (m, 2H), 2.05-2.12(m, 1H), 1.98-2.04 (m, 1H), 1.28 (s, 3H), 1.17 (d, J=8.6 Hz, 1H), 0.84 (s, 3H).

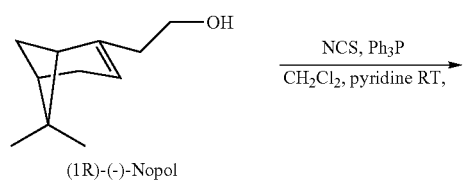

(1R)-(-)-Nopol

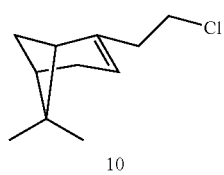

10

Pinene Chloride 10: Pinene chloride 10 was prepared as a colorless oil in the same manner as described for pinene bromide 11 except that N-chlorosuccinimide (NCS) was substituted for N-bromosuccinimide. (4.2 g, 95%). IR (CHCl$_3$): 2993, 2924, 2838, 1450, 1387, 1370, 1297, 1267, 1120, 1100, 1085, 958 and 888 cm$^{-1}$. $^1$HNMR (400 MHz, CDCl$_3$): δ 5.34 (s with fine splittings, 1H), 3.46-3.57 (m, 2H), 2.34-2.47 (m, 3H), 2.16-2.34 (m, 2H), 2.06-2.14 (m, 1H), 2.03 (dt J=1.5, 5.6 Hz, 1H), 1.29 (s, 3H), 1.17 (d, J=8.7 Hz, 1H), 0.85 (s, 3H).

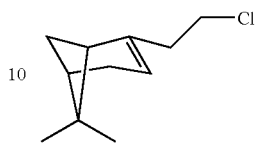

10

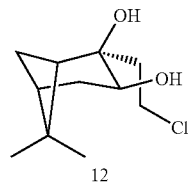

12

Pinanediol Chloride 12: To a mixture of 4-methylmorpholine-N-oxide (NMO, 2.6 g, 22 mmol, 1.05 equiv), t-butanol (45 ml), water (8 ml) and hexamethylenetetraamine (HMTA, 4.1 g, 29 mmol, 1.4 equiv), pinene chloride 10 (3.9 g, 21 mmol) and osmium tetroxide stock solution (40 mg/ml H$_2$O, 1.7 ml. 0.26 mmol, 0.0125 equiv) were added at room temperature under an argon atmosphere. The resulting light tan mixture was heated to <55° C. for 6 hours. After cooling to room temperature, the mixture was quenched with 40 ml of 10% NaHSO$_3$ solution and stirred for 30 minutes. The aqueous solution was extracted three times with 30% EtOAc/hex. The combined organic extracts were washed with brine and water, dried over anhydrous Na$_2$SO$_4$ and concentrated to afford the crude product as a dark tan oil. The crude product was purified by silica gel chromatography, eluting first with hexanes to recover the unreacted starting material 10 as a colorless oil (2.1 g, 54%). The column was further eluted with 10~25% EtOAc/hex, and the clean fractions were pooled and concentrated to give a tan solid. The product was crystallized in hexanes to give the 1$^{st}$ crop of pinanediol chloride 12 as white crystalline plates (1.3 g, 29%). The mother liquor and the impure fractions were pooled and repurified to give the 2$^{nd}$ crop of diol 12 (0.43 g, 9.4%). IR (CHCl$_3$): 3617, 3515, 3004, 2930, 2876, 1455, 1374, 1110, 1042, 1012, 946, 910 and 657 cm$^{-1}$. $^1$H NMR (400 MHz, CDCl$_3$): δ 4.15 (dt, J=9.6, 5.9 Hz, 1H), 3.80 (ddd, J=11, 8.4, 5.6 Hz, 1H), 3.73 (ddd, J=10.9, 8.6, 5.8 Hz, 1H), 3.13 (s, OH, 1H), 2.68 (d, J=6.2 Hz, OH, 1H), 2.47-2.57 (m, 1H), 2.09-2.29 (m, 3H), 1.93-2.04 (m, 2H), 1.64-1.67 (m, 1H), 1.38 (d, J=10.2 Hz, 1H), 1.30 (s, 3H), 0.99 (s, 3H).

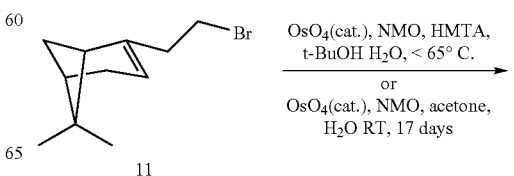

11

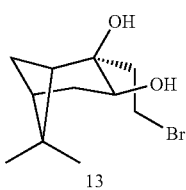

Pinanediol Bromide 13: A mixture of 4-methylmorpholine N-oxide (NMO, 1.1 g, 9.2 mmol, 1.05 equiv), t-butanol (18.5 ml), water (3.3 ml), hexamethylenetetraamine (3.4 g, 24 mmol, 2.8 equiv), pinene bromide 11 (2 g, 8.7 mmol), and osmium tetroxide stock solution (40 mg/ml H$_2$O, 0.7 ml. 0.11 mmol, 0.0125 equiv) was heated at 70° C. for 18.5 hours under argon atmosphere. TLC of the resulting dark brown mixture showed no product spot. When the reaction was run under milder conditions with a shorter reaction time by heating the mixture of 4-methylmorpholine-N-oxide (NMO, 805 mg, 6.9 mmol, 1.05 equiv), t-butanol (14 ml), water (2.6 ml), hexamethylenetetraamine (HMTA, 1.3 g, 24 mmol, 1.4 equiv), pinene bromide 11 (1.5 g, 6.5 mmol), and osmium tetroxide stock solution (40 mg/ml H$_2$O, 0.52 ml. 0.08 mmol, 0.0125 equiv) at <65° C. for 6.5 hours under an argon atmosphere, the product was isolated as an orange gum (905 mg, 53%) in addition to recovered starting material (334 mg, 22%). The pinanediol bromide 13 did not solidify in hexanes, and was shown to contain a long contaminant tail underneath the pinanediol bromide 13 by TLC.

However, the clean pinanediol bromide 13 could be obtained by employing dihydroxylation reaction conditions for unhindered alkenes without HMTA. A mixture of 4-methylmorpholine-N-oxide (NMO, 309 mg, 2.6 mmol, 1.2 equiv), acetone/water (9:1, 15 ml), pinene bromide 11 (503 mg, 2.2 mmol), and osmium tetroxide stock solution (40 mg/ml H$_2$O, 0.07 ml. 11.7 μmole, 0.05 equiv) was stirred at room temperature for 17 days. After standard workup, pinanediol bromide 13 was obtained as an off-white crystalline solid (435 mg, 75%). IR (CHCl$_3$): 3617, 3490, 3004, 2927, 2888, 1452, 1373, 1256, 1107, 1040, 1026, 957, 907 and 645 cm$^{-1}$. $^1$HNMR (400 MHz, CDCl$_3$): δ 4.08-4.15 (m, 1H), 3.51-3.66 (m, 2H), 3.03 (s, OH, 1H), 2.62 (d, J=6.2 Hz, OH, 1H), 2.48-2.57 (m, 1H), 2.20-2.30 (m, 2H), 2.04-2.15 (m, 2H), 1.92-1.99 (m, 1H), 1.66 (ddd, J=14.2, 5.2, 2.5 Hz, 1H), 1.37 (d, J=10.3 Hz, 1H), 1.30 (s, 3H), 0.98 (s, 3H).

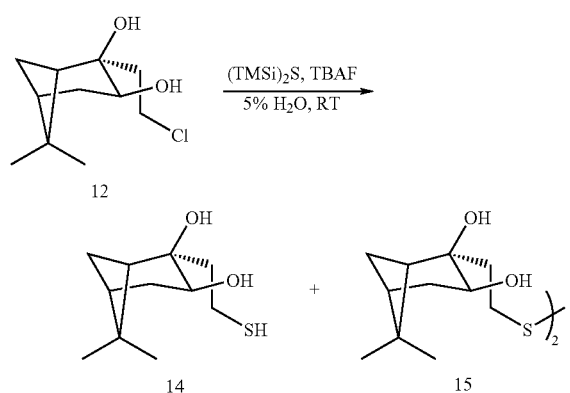

Pinanediol Thiol 14 and Disulfide 15: To a solution of pinanediol chloride 12 (300 mg, 1.4 mmol) in anhydrous THF (2.7 ml), hexamethyldisilathiane ([TMSi]$_2$S, 0.35 ml, 1.6 mmol, 1.2 equiv) was added at −5° C. under argon atmosphere. The resulting mixture was then treated with 1 M solution of tetrabutylammonium fluoride (TBAF, 1.5 ml, 1.5 mmol, 1.1 equiv) in tetrahydrofuran (THF), containing 5% of water. The color of the mixture changed from yellow to green during the addition of TBAF. The reaction remained incomplete after 5 hours of stirring at room temperature. Saturated NH$_4$Cl solution was added, the mixture was then extracted 3 times with 50% EtOAc/hex. The combined organic extract was washed with saturated NaHCO$_3$ solution, and dried over anhydrous Na$_2$SO$_4$. The organic solution was filtered through a silica gel plug, eluting with 0~4% MeOH in CH$_2$Cl$_2$, to give a colorless gum (284 mg) as a mixture of unreacted starting material chloride 12, thiol 14 and disulfide 15. Unlike the protected acetonide analogue, the thiol 14 and disulfide 15 were inseparable by silica column. The assignment of 14 and 15 was based on TLC and $^1$H NMR spectrum. Thiol 14 showed a characteristic blue stain instantly on the TLC plate at room temperature when contacted with a 10% solution of phosphomolybdic acid (PMA) in MeOH; the stain of the disulfide 15 was visualized only after the plate was heated. In the $^1$H NMR spectrum, the signal multiplicity from the methylene protons on the carbon bearing the sulfur atom should be more complex for thiol 14 than disulfide 15, due to the extra vicinal coupling to the thiol proton. The methylene signals appeared at 2.72 ppm (m, 5 lines, 2H) and 2.87 ppm (m, 4 lines, 2H) for thiol 14 and disulfide 15, respectively. The ratio of the starting material 12, thiol 14 and disulfide 15 was estimated as 1.4:1:3.5, based on the integrals of one of the geminal methyl protons at 0.98, 0.976 and 0.96 ppm respectively.

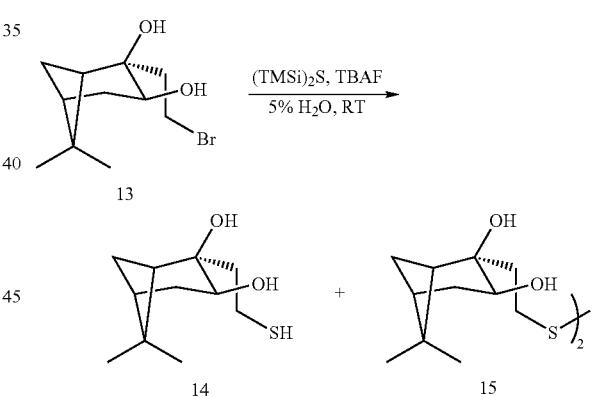

Pinanediol Thiol 14 and Disulfide 15: A mixture (275 mg) of thiol 14 and disulfide 15 in a 1.68:1 ratio was also obtained by the same reaction with pinanediol bromide 13 (335 mg, 1.3 mmol), [TMSi]$_2$S (0.32 ml, 1.5 mmol, 1.2 equiv) and IM TBAF solution (1.4 ml, 1.4 mmol, 1.1 equiv) in THF containing 5% water. The reaction was complete after 2 hours of stirring at room temperature. The thiol 14 was the predominate product in this faster reaction, as opposed to the slow reaction with chloride 12.

Contemplated Synthesis of Pinanediol w/C11 Thiol Linker or w/Ether C8 Thiol Linker (Prophetic Example)

The present teachings also contemplate adaptation of the preceding methods to construct pinanediols with a linker thiol of C5-C16 chain length for surface modification of gold via self-assembled monolayers (SAMs). Chain elongation of nopylhalides (e.g., such as compound 11) to a C6-C12 derivative, followed by oxidation to the pinanediol derivative, and conversion of the C6-C12 side chain to an alkyl sulfide and/or disulfide, exemplifies the general synthetic method contemplated for pinanediol thiol linker compounds of the general formula:

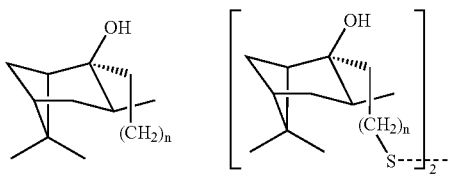

In some embodiments, SAM surfaces can be generated from thiols. In some embodiments, SAM surfaces can be generated from the disulfide. In some embodiments, SAM surfaces can be generated from mixtures of thiol and disulfide.

Disulfide cis-diols can be converted to the sulfide analogues just prior to SAM surface modification by reaction of the disulfide with tris(2-carboxyethyl)phosphine hydrochloride (TCEP.HCl). TCEP.HCl is a water-soluble reducing agent that exhibits better stability and more effective reductive capability than dithiothreitol (DTT) or 2-mercaptoethanol. The agent retains its reductive activity in a broad pH range (pH 5 to >pH 7.5) and typically can be used in a molar excess quantity. An example of disulfide reduction immediately prior to SPR detection is reduction by TCEP.HCl of thiolated-ssDNA just before application to bare Au surfaces.

CONJUGATION EXAMPLES

Conjugation Example 1

Pinanediol/m-Dansylaminophenylboronic Acid

FIG. 1 is a schematic of covalent conjugation of surface-bound pinane acetonide (bound to poly-D-Lys Plates) with borate (m-dansylaminophenylboronic acid). Two sets of triplicates were run in 96-well, poly-D-lysine coated polystyrene plates (Sigma M 5682, Sigma-Aldrich, St. Louis, Mo.). The 70-150 kDa polymer provides a uniform net of positively charged ammonium groups, which were neutralized with $NaHCO_3$ washes (×3, pH 7) to primary amines and coupled with the pinane acetonide NHS ester (1 hr). (Pinane acetonide NHS ester was synthesized by TSTU activation and isolated as a precipitate for use in the coupling reaction.) The covalently attached pinane acetonide was then deprotected to the pinanediol with a 1:1 $TFA/H_2O$ incubation (2 hrs). After neutralization washes (dil $NaHCO_3$ ×1, $H_2O$ ×1), incubation of the pinanediol modified wells with m-dansylaminophenylboronic acid (5 mM in EtOH, M Probes D-2281, Molecular Probes, Inc. Eugene, Oreg.), followed by EtOH washes to remove residual, uncomplexed boronic acid, resulted in dansyl fluorescence at 530 nm (ex 360 nm) with S/N=8. Control wells containing 5 mM dansylaminophenylboronic acid, followed by removal of the fluorophore solution and EtOH washes (×3) showed a 50% increase over background (blank wells).

Figure 2:
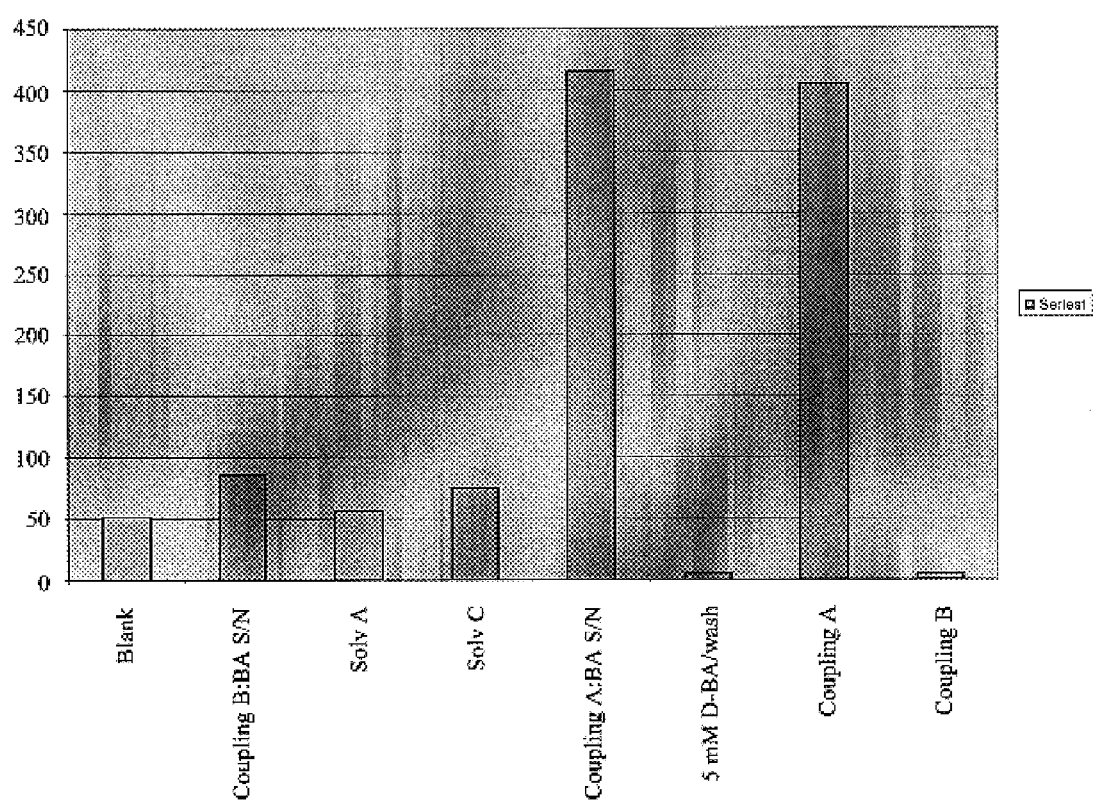
FIG. 2 shows the fluorescence signal and signal-to-noise ratios in control wells (originally containing the DAPB acid solution) and wells containing pinane diol (bound to poly-D-Lys Plates) conjugated to DAPB.

FIG. 2 shows the fluorescence signal and signal-to-noise ratios in control wells (originally containing the dansylaminophenylboronic acid solution) and wells containing pinane diol (bound to poly-D-Lys Plates) conjugated to borate (m-dansylaminophenylboronic acid). In FIG. 5, "blank" is the signal for an empty well; "Solvent A" is the signal for a well containing ethanol; "Solvent C" is the signal for a well containing 20% $H_2O/CH_3CN$; and "5 mM D-BA/wash" is the signal for a blank well washed with -dansylaminophenylboronic acid in EtOH, followed by 3× EtOH washes, with EtOH added for analysis. The columns "coupling A" and "coupling B" are the signal for wells where pinane acetonide NHS ester is covalently attached in solvent C to a well, washed w/solvent C ×2 followed by $TFA/H_2O$ incubation, then washed w/dil $NaHCO_3$ ×1, washed w/$H_2O$ ×1, incubated w/5 mM m-dansylaminophenylboronic acid in EtOH, followed by 3× EtOH washes, and EtOH is added for analysis. The columns "coupling A:BA S/N" and "coupling B:BA S/N" are the signal to noise ratios of the respective conjugated wells versus the respective solvent-washed blank wells. These signal to noise ratios ranged from about 5.33 to about 5.46.

Conjugation Example 2

Constrained cis-diol/borate Conjugation for SPR

On a bare gold surface plasmon resonance chip (available for Affinity Chip SPR Analyzer model 8500, Applied Biosystems, Foster City, Calif.), constrained diol ((1R,2R,3S,5R)-2-(2-mercaptoethyl)-6,6-dimethylbicyclo[3.1.1]heptane-2,3-diol):

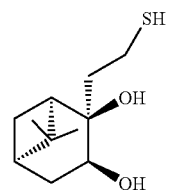

was spotted using was spotted on a MicroSys spotter (Cartesian Dispensing Systems, presently Genomic Solutions) with a SMP 10B pin (Telechem), in phosphate buffered saline (PBS) with less than about 1% dimethylformamide (DMF). Concentrations of about 1, 5, 25, 100, and 200 μM were spotted in the presence and absence of 1 mM tris (2-carboxylethyl) phosphine (TCEP). TCEP is typically used in place of dithiothreitol (DTT) as a non thiol-based reductant. Controls of bovine serum albumin (BSA) and PBS with 1 mM TCEP were also spotted. All solutions were spotted in replicates of nine. The chip was then incubated in a humid environment for about 1 hour.

After spotting, the chip was assembled, loaded onto the SPR analyzer, and individual reference spots were assigned adjacent to the left of spotted material. The chip was blocked with about 10 mL of 0.5 mM capped mercapto-PEG-2000. PBS with 0.05% Tween-20 (PBST), was used to equilibrate the chip for 60 minutes at a flow rate of 0.5 mL/min in order to minimize drift effects.

A solution of 3.5 mL m-dansylaminophenylboronic acid (DAPB, molecular weight 370.23 g/mol, catalog number D-2281, Molecular Probes, Eugene, Oreg.):

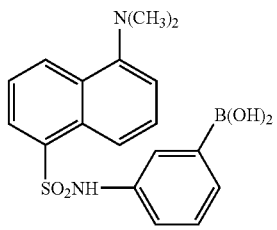

20 µM in PBST, was allowed to re-circulate over the equilibrated chip for 30 minutes at a flow rate of 0.5 mL/min. During this time association of DAPB could be observed with the constrained diol spotted at 25 µM. Dissociation was allowed to take place over a period of 30 minutes with a flow rate of 0.5 mL/min.

Results

Figure 3:
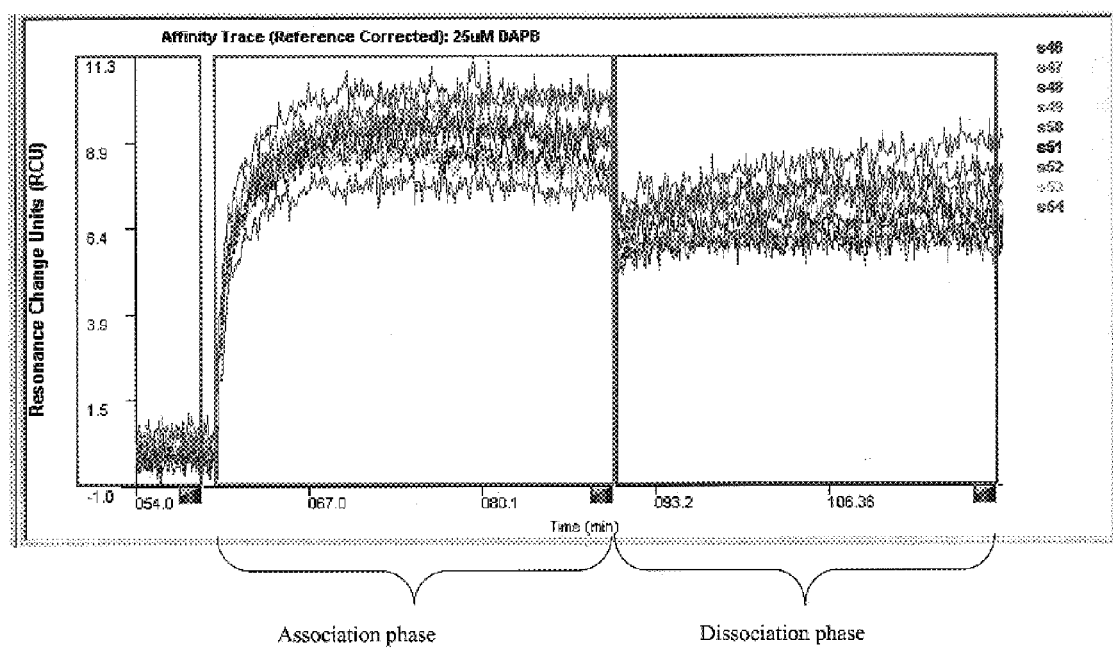
FIG. 3 shows binding curves for 20 µM DAPB binding to immobilized constrained diol 14 at concentrations of 25 µM.

FIG. 3 shows binding curves could be observed for 20 µM DAPB binding to the immobilized constrained diol at concentrations of 25 µM.

Figure 4:
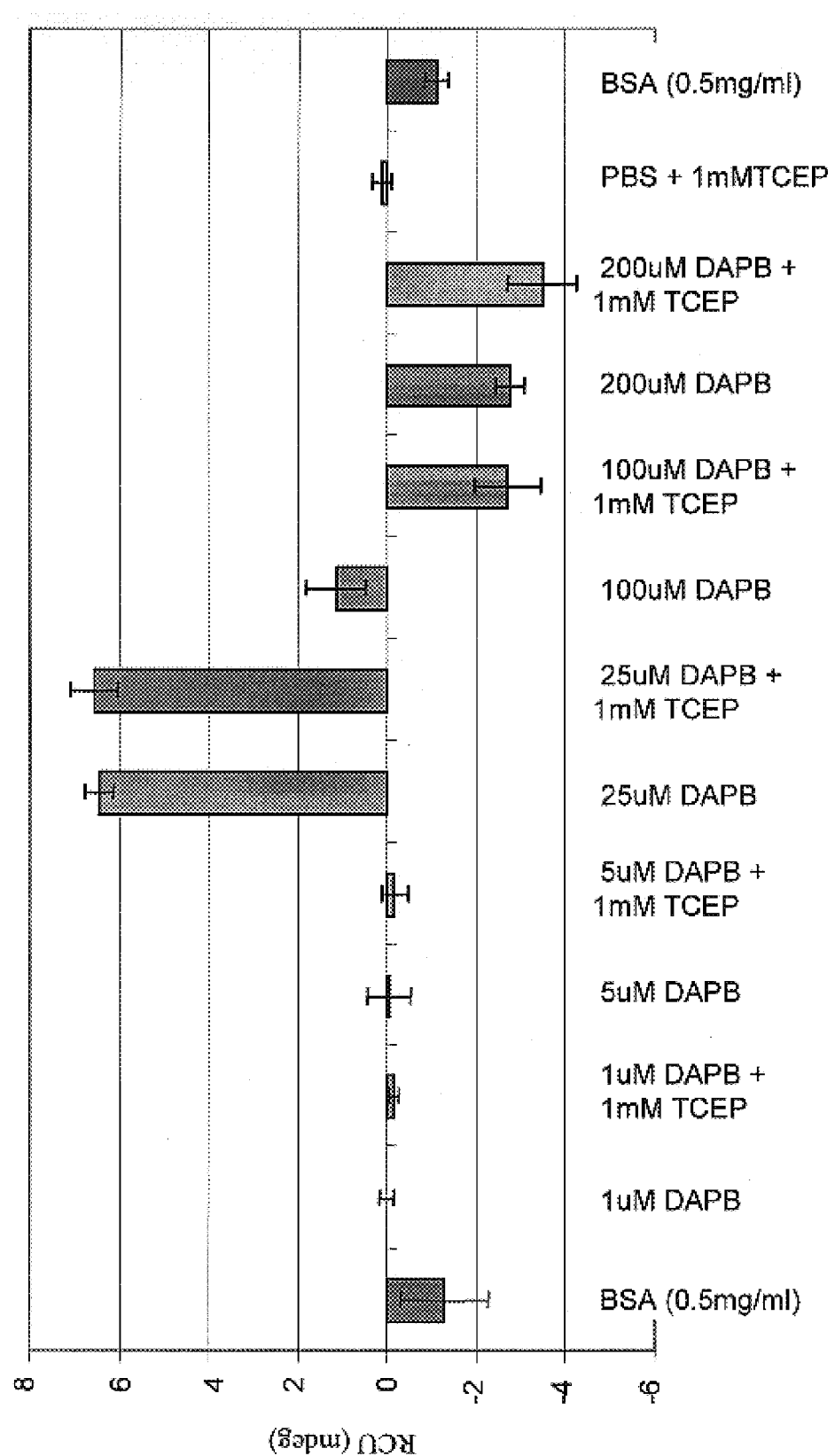
FIG. 4 shows the presence or absence of tris (2-carboxylethyl) phosphine (TCEP) did not appear to have a significant effect upon end-point binding. At concentrations of 1 and 5 µM, no binding above background levels was observed. Beginning at concentrations of 100 µM DAPB, a detrimental effect upon binding at the higher spotted densities of constrained diol 14 was observed.

FIG. 4 shows the presence or absence of TCEP did not appear to have a significant effect upon end-point binding. At the lower concentrations of 1 and 5 µM, no binding above background levels could be observed. Beginning at concentrations of 100 µM DAPB, a detrimental effect upon binding at the higher spotted densities of the constrained diol was observed.

Two reasons can account for this effect. At the higher densities over-saturation of the gold surface can occur. The presence of binding to adjacent reference spots suggested this outcome. Also, at very high densities, a tightly packed layer of constrained diol can hinder the reaction of DAPB. The negative end-point signal at 200 µM spotted constrained diol indicates that binding to the reference spots is greater than binding to the densely spotted material (FIG. 2).

Figure 5A:
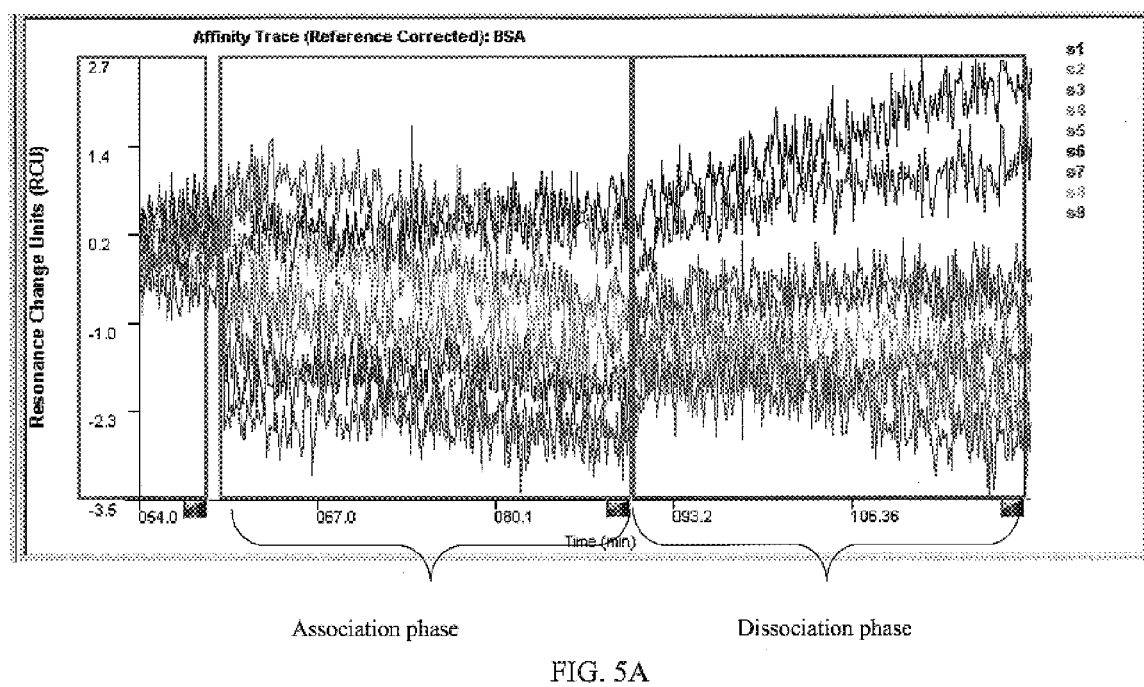
FIGS. 5A and 5B show negative controls (bovine serum albumin, (BSA) and phosphate buffer saline (PBS) with 1 mM TCEP that show no DAPB binding.
Figure 5B:
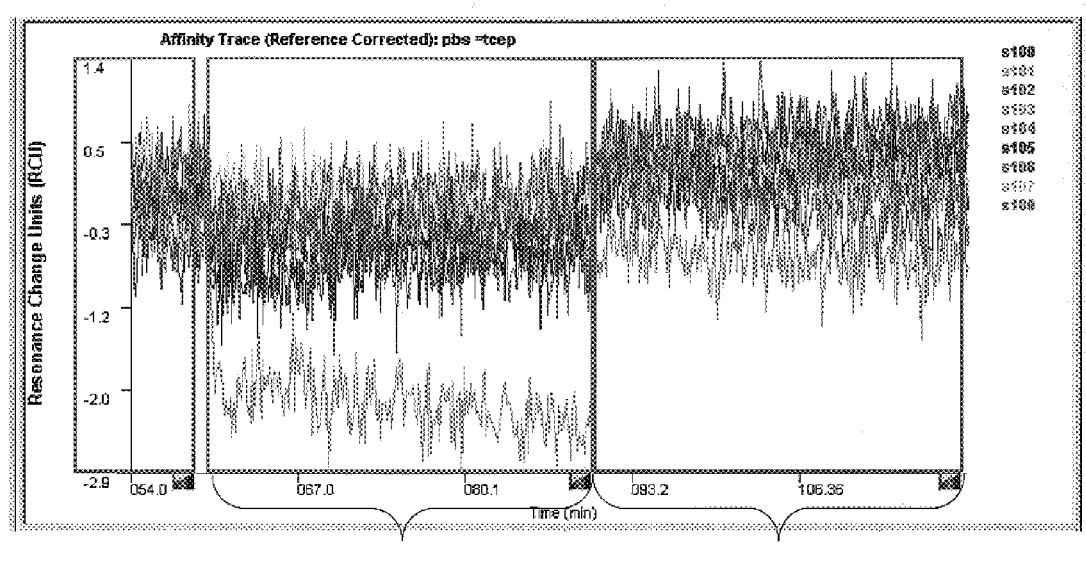

FIGS. 5A and 5B show that both negative controls (BSA and PBS with 1 mM TCEP) exhibited no DAPB binding.

The binding of DAPB to immobilized constrained diol has been observed in three separate experiments. The SPR results suggest that a real binding event for a small molecule was observed. The high density surface afforded by constrained diol may account for the ability to detect a 370 Dalton species by the 8500 systems under flow. The smallest analyte detected previously under flow using this particular SPR analyzer was a peptide of about 1000 Daltons.

The association rate of DAPB with constrained diol can seem slow. Detailed kinetic analyses were not possible but the association rate appears to be in order of ~10E2 $M^{-1}s^{-1}$. Steric problems may potentially explain the slow association. Dissociation, on the other hand, appears to be slow and blends in with the instrument drift (some of the dissociation curves appear to drift up).

Conjugation Example 3

Constrained borate/cis-diol Conjugation for SPR

On a bare gold surface plasmon resonance chip (available for Affinity Chip SPR Analyzer model 8500, Applied Biosystems, Foster City, Calif.), 4-mercaptophenylboronic acid (Aldrich, St. Louis, Mo.) was spotted on a MicroSys spotter (Cartesian Dispensing Systems, presently Genomic Solutions) with a SMP 10B pin (Telechem), in phosphate buffered saline (PBS) with 50% ethanol. Concentrations of about 100, 200, and 500 µM were spotted. All solutions were spotted in replicates of three. The chip was then incubated in a humid environment for about 1 hour.

After spotting, the chip was assembled, loaded onto the SPR analyzer, and individual reference spots were assigned adjacent to the left of spotted material. The chip was blocked with 1 mM capped mercapto-PEG-2000. Buffer solution, either PBST (phosphate buffer saline (PBS), pH 7.4 with 0.05% Tween-20), sodium acetate buffer (50 mM sodium acetate, 100 mM sodium chloride, pH 5.5), or carbonate buffer (200 mM sodium carbonate-bicarbonate, pH 9.4), was used to equilibrate the chip for 60 to 90 minutes at a flow rate of 0.5 mL/min in order to minimize drift effects.

A solution of 2.5 mL pinanediol acetate:

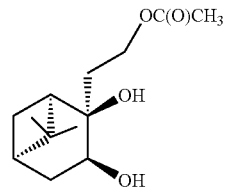

100 µM in PBST, sodium acetate buffer, or carbonate buffer was allowed to re-circulate over the equilibrated chip for 30 to 60 minutes at a flow rate of 0.5 mL/min. During this time, association of pinanediol acetate could be observed with the immobilized 4-mercaptophenylboronic acid. Dissociation was allowed to take place over a period of 30 minutes with a flow rate of 0.5 mL/min.

Results

Figure 6A:
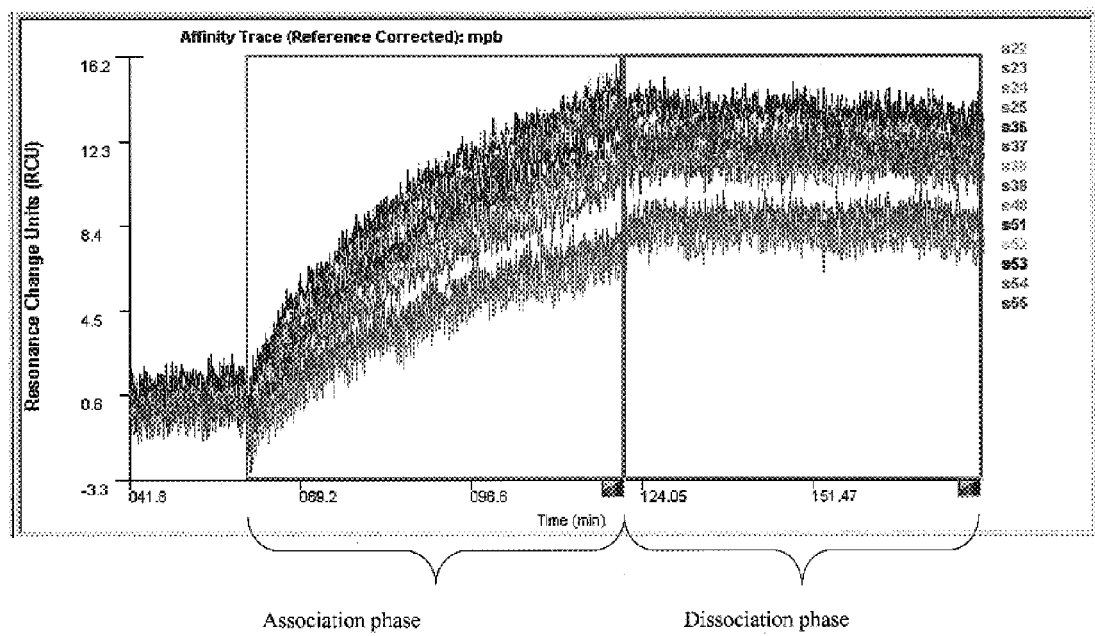
FIGS. 6A-C show affinity traces observed for 100 µM pinanediol acetate binding to immobilized 4-mercaptophenylboronic acid under various buffer conditions.

FIG. 6A shows affinity traces observed for 100 µM pinanediol acetate binding to the immobilized 4-mercaptophenylboronic acid. The buffer used was 50 mM sodium acetate, 100 mM sodium chloride, pH 5.5.

Figure 6B:
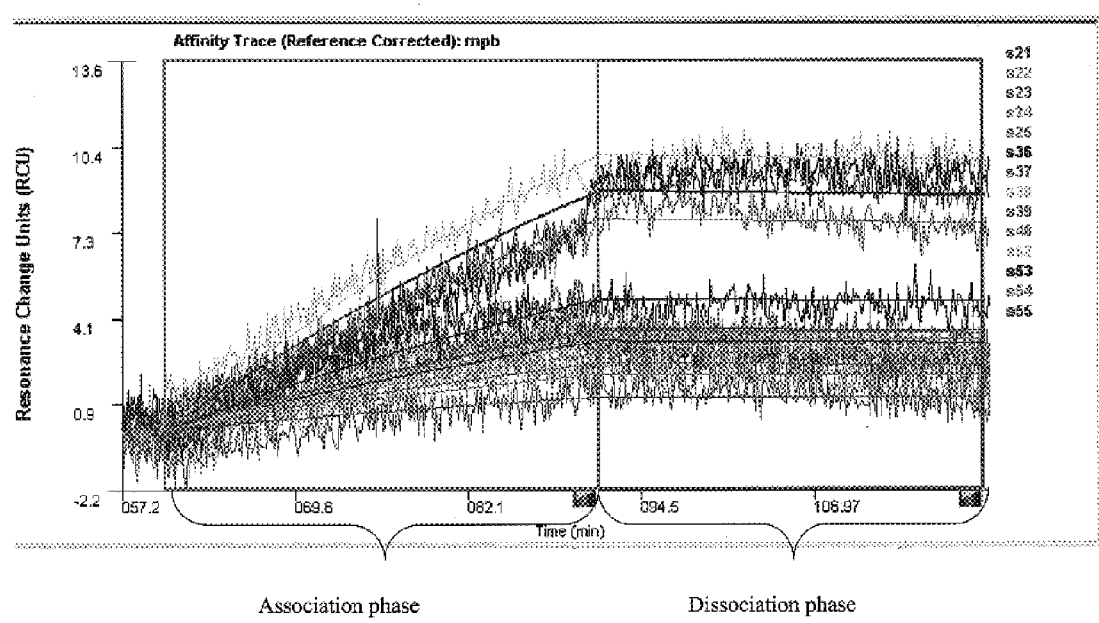

FIG. 6B shows affinity traces observed for 100 µM pinanediol acetate binding to the immobilized 4-mercaptophenylboronic acid. The buffer used was phosphate buffered saline with 0.05% Tween-20, pH 7.4.

Figure 6C:
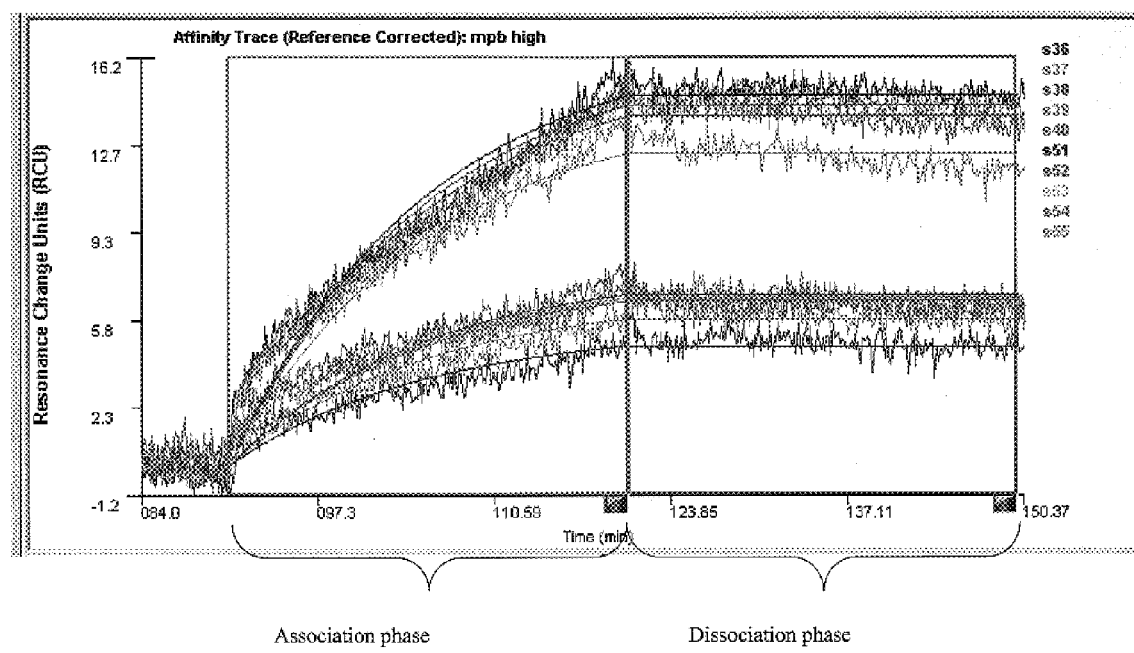

FIG. 6C shows affinity traces observed for 100 µM pinanediol acetate binding to the immobilized 4-mercaptophenylboronic acid. The buffer used was sodium carbonate-bicarbonate buffer pH 9.4.

This set of experiments demonstrates that the cis-diol-borate conjugation can be achieved by first immobilizing the borate-containing compound, and then capturing the constrained cis-diol derivative under flow. The conjugation was observed at pH 5.5, pH 7.4, and pH 9.4. In all cases, the dissociation rate was less than $10^{-5}$ $s^{-1}$ and could not reliably measured relative to the instrument and/or surface drift rate. The association rates observed were less than or equal to 10 $M^{-1}s^{-1}$.

The section headings used herein are for organizational purposes only and are not to be construed as limiting the subject matter described in any way.

All literature and similar materials cited in this application, including but not limited to, patents, patent applications, articles, books, treatises, and internet web pages, regardless of the format of such literature and similar materials, are expressly incorporated by reference.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

What is claimed is:

1. A bioconjugation system, comprising a sterically constrained cis-diol and a borate represented respectively by:

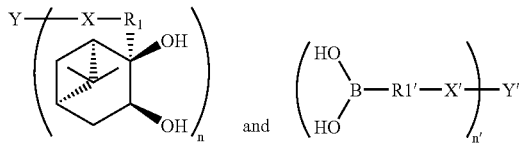

wherein:
$R^1$ is C2-C16 alkyl ether, C1-C16 alkoxy or C1-C16 alkyl;
$R^1$ is an aryl, aralkyl, C1-C16 alkyl, or C1-C16 alkoxy group;
wherein the cis-diol and borate are bonded through the hydroxyl groups to form a conjugate represented by:

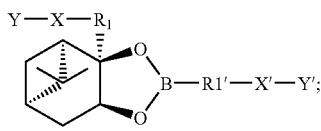

X is —NH—, —C(O)NH—, —NHC(O)— or —S—;
X' is a bond, —O—, —S—, —C(O)—, —C(O)O—, —S(O)—, —OSO$_2$—, —S(O$_2$)O—, —SO$_2$—, —NR$^3$—, —NR$^3$C(O)—, —C(O)NR$^3$C—, —R$^3$NNR$^3$SO$_2$—, —SO$_2$NR$^3$NR$^3$—, —NR$^3$SO$_2$—, —SO$_2$NR$^3$—, —CR$^3{}_2$C(O)NR$^3$—, —NR$^3$C(O)CR$^3{}_2$—, —CR$^3{}_2$C(O)—, —C(O)CR$^3{}_2$—, —R$^3$NNR$^3$—, —NR$^3$NR$^3$—, —R$^3$NNR$^3{}_2$—, —NR$^3{}_2$NR$^3$—, —CR$^3{}_2$Ph—, —PhCR$^3{}_2$—, —C(NR$^3$)NR$^3$—, or —NR$^3$C(NR$^3$)—;
each $R^3$ is independently —H, alkyl, alkoxy, aryloxy or arylalkoxy;
Y is a solid support;
Y' is a bioactive molecule comprising one or more peptides;
n is an integer from 10 to $10^{10}$; and
n' is an integer from 1 to 200.

2. The system of claim 1, wherein n' is 1.

3. The system of claim 2, wherein in aqueous 0.10 M phosphate buffer at 25° C. and pH 7.4, the conjugate has a dissociation rate of less than about $1\times10^4 s^{-1}$.

4. The system of claim 2, wherein the solid support comprises gold, silver, platinum, aluminum, or copper.

5. The system of claim 2, wherein the solid support is in the form of a bead, a microsphere, nanoparricle, gel, membrane, surface, film, porous matrix, or interior surface of a microchannel.

6. The system of claim 2, wherein the solid support is a nanoparticle comprising cadmium sulfide, cadmium selenide, cadmium telluride, silicon, or gallium arsenide.

7. The system of claim 2, wherein the solid support comprises optionally substituted polyalkylene, polyvinylene, polystyrene, polyethylene oxide, nitrocellulose, polyvinyl acetate, polyvinyl chloride, polyvinyl dichloride, polyfluoroalkylene, polyamide, polydialkylsiloxane, glass, silica, or quartz.

8. The system of claim 2, wherein the solid support has a conductive layer for surface plasmon resonance.

9. The system of claim 2, wherein X is —S— and $R^1$ is —(CH$_{22}$O(CH$_2$)$_8$— or —(CH$_2$)$_{11}$—.

10. The system of claim 2, wherein the cis-diol and borate form a stable conjugate represented by:

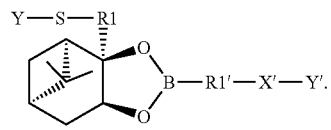

11. The system of claim 2, wherein $R^1$ is C6-C12 alkyl.
12. The system of claim 2, wherein $R^1$ is C1-C3 alkyl.
13. The system of claim 12, wherein the cis-diol and borate form a stable conjugate represented by:

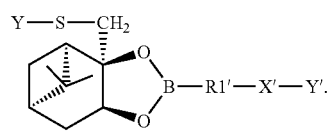

14. The system of claim 2, wherein the cis-diol and borate form a stable conjugate represented by:

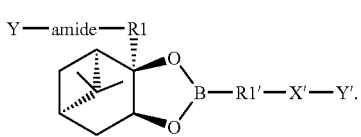

15. The system of claim 14, wherein the cis-diol and borate form a stable conjugate represented by:

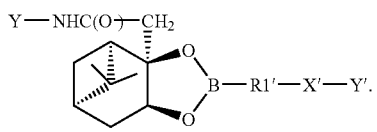

16. The system of claim 1, further comprising a plurality of each of the sterically constrained cis-diols and the borates; wherein:
Y' is for each corresponding borate, a distinct bioactive molecule selected from a plurality of distinct bioactive molecules; and
each corresponding n' is an integer from 1 to 3,
whereby the bioconjugation system comprises a library of distinct bioactive molecules.

17. The system of claim 16, wherein each bioactive molecule has a molecular weight between about 50 and about 5000 daltons.

18. The system of claim 17, wherein each bioactive molecule is a product of chemical synthesis or combinatorial synthesis.

19. The system of claim 18, wherein:
Y' is independently for each borate, a distinct bioactive molecule;
Y is independently for each cis-diol, a spatially distinct reaction site in an array; and
n' is 1.

20. A method of preparing a conjugate represented by:

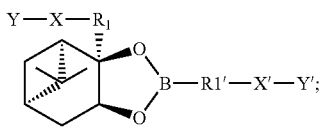

comprising reacting a sterically constrained cis-diol and a borate represented respectively by:

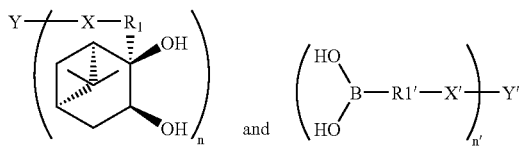

under conditions suitable for reaction between the constrained cis-diol and the borate, thereby forming the conjugate, wherein:
$R^1$ is C2-C16 alkyl ether, C1-C16 alkoxy or C1-C16 alkyl;
$R^1$ is an aryl, aralkyl, C1-C16 alkyl, or C1-C16 alkoxy group;
X is —NH—, —C(O)NH—, —NHC(O)— or —S—;
X' is a bond, —O—, —S—, —C(O)—, —C(O)O—, —S(O)—, —OSO$_2$—, —S(O$_2$)O—, —SO$_2$—, —NR$^3$—, —NR$^3$C(O)—, —C(O)NR$^3$C—, —R$^3$NNR$^3$SO$_2$—, —SO$_2$NR$^3$NR$^3$—, —NR$^3$SO$_2$—, —SO$_2$NR$^3$—, —CR$^3{}_2$C(O)NR$^3$—, —NR$^3$C(O)CR$^3{}_2$, —CR$^3{}_2$C(O)—, —C(O)CR$^3{}_2$—, —R$^3$NNR$^3$—, —NR$^3$NR$^3$—, —R$^3$NNR$^3{}_2$—, —NR$^3{}_2$NR$^3$—, —CR$^3{}_2$Ph—, —PhCR$^3{}_2$—, —C(NR$^3$)NR$^3$—, or —NR$^3$C(NR$^3$)—;
each $R^3$ is independently —H, alkyl, alkoxy, aryloxy or arylalkoxy;
Y is a solid support;
Y' is a bioactive molecule comprising one or more peptides;
n is an integer from 10 to $10^{10}$; and
n' is an integer from 1 to 200.

21. The method of claim 20, wherein n' is 1.

22. The method of claim 21, wherein in aqueous 0.10M phosphate butter at 25° C. and pH 7.4, the conjugate has a dissociation rate of less than about $1 \times 10^4 s^{-1}$.

23. The method of claim 21, wherein the solid support comprises gold, silver, platinum, aluminum, or copper.

24. The method of claim 21, wherein the solid support is in the form of a bead, a microsphere, nanoparticle, gel, membrane, surface, film, porous matrix, or interior surface of a microchannel.

25. The method of claim 21, wherein the solid support is a nanoparticle comprising cadmium sulfide, cadmium selenide, cadmium relluride, silicon, or gallium arsenide.

26. The method of claim 21, wherein the solid support comprises optionally substituted polyalkylene, polyvinylene, polystyrene, polyethylene oxide, nitrocellulose, polyvinyl acetate, polyvinyl chloride, polyvinyl dichloride, polyfluoroalkylene, polyamide, polydialkylsiloxane, glass, silica, or quartz.

27. The method of claim 21, wherein the solid support includes a conductive layer for surface plasmon resonance.

28. The method of claim 27, further comprising constructing an array by preparing the conjugate at a plurality of spatially distinct reaction sites on the solid support.

29. The method of claim 28, wherein each spatially distinct reaction site in the array has an average diameter of between about 5 μm and about 1000 μm.

30. The method of claim 28, wherein the spatially distinct reaction sites in the array are in a surface density of between about 12 sites per cm$^2$ and about 50,000 sites per cm$^2$.

31. The method of claim 30, further comprising preparing the conjugate at two or more reaction sites in the array to be compositionally distinct by:
  contacting a first site with the cis-diol or the borate having the bioactive molecule, in an amount distinct from that employed at a second site; or
  contacting a first site with a first cis-diol or borate containing a first bioactive molecule and contacting a second site with a second cis-diol or borate containing a second bioactive molecule.

32. The method of claim 31, further comprising determining the extent of conjugation at the first and the second site.

33. The method of claim 21, wherein X is —S— and $R^1$ is —(CH$_2$)$_2$O(CH$_2$)$_8$— or —(CH$_2$)$_{11}$—.

34. The method of claim 21, wherein the cis-diol and borate form a stable conjugate represented by:

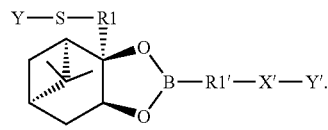

35. The method of claim 34, wherein $R^1$ is C6-C12 alkyl.

36. The method of claim 34, wherein $R^1$ is C1-C3 alkyl.

37. The method of claim 36, wherein the cis-diol and borate form a stable conjugate represented by:

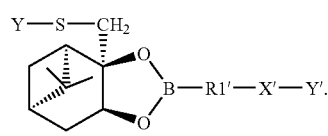

38. The method of claim 21, wherein the cis-diol and borate form a stable conjugate represented by:

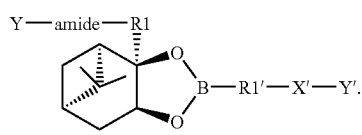

39. The method of claim 38, wherein the cis-diol and borate form a stable conjugate represented by:

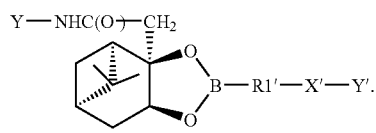

40. The method of claim 20, further comprising a plurality of each of the sterically constrained cis-diols and the borates; wherein:

Y' is for each corresponding borate, a distinct bioactive molecule selected from a plurality of distinct bioactive molecules; and each corresponding n or n' is an integer from 1 to 3, whereby the bioconjugation system is prepared as a library of distinct bioactive molecules.

41. The method of claim 40, wherein each distinct bioactive molecule has a molecular weight between about 50 and about 5000 daltons.

42. The method of claim 41, wherein each distinct bioactive molecule is a product of chemical synthesis or combinatorial synthesis.

43. The method of claim 42, further comprising:

combining a target molecule with each distinct bioactive molecule.

44. The method of claim 43, wherein:

Y' is independently for each borate, a distinct bioactive molecule;

Y is independently for each cis-diol, a spatially distinct reaction site in an at-ray, and n' is 1.

* * * * *